United States Patent
Escutia et al.

(10) Patent No.: US 8,801,631 B2
(45) Date of Patent: *Aug. 12, 2014

(54) DEVICES AND METHODS FOR FACILITATING FLUID TRANSPORT

(75) Inventors: Raul Escutia, Palo Alto, CA (US); Jeffrey Lorne Emery, Redwood City, CA (US)

(73) Assignee: Intuity Medical, Inc., Sunnyvale, CA (US)

( * ) Notice: Subject to any disclaimer, the term of this patent is extended or adjusted under 35 U.S.C. 154(b) by 489 days.

This patent is subject to a terminal disclaimer.

(21) Appl. No.: 11/239,123

(22) Filed: Sep. 30, 2005

(65) Prior Publication Data
US 2007/0078358 A1 Apr. 5, 2007

(51) Int. Cl.
*A61B 5/157* (2006.01)
*A61B 5/155* (2006.01)
*A61B 5/151* (2006.01)
*A61B 5/15* (2006.01)

(52) U.S. Cl.
USPC ............................. 600/583; 600/584; 606/181

(58) Field of Classification Search
USPC ................................... 600/583, 584; 606/181
See application file for complete search history.

(56) References Cited

U.S. PATENT DOCUMENTS

| 842,690 A | 1/1907 | Oswalt |
| D137,874 S | 5/1944 | Partridge |
| 2,749,797 A | 3/1950 | Harks |
| 3,092,465 A | 6/1963 | Adams, Jr. |
| 3,310,002 A | 3/1967 | Wilburn |
| 3,620,209 A | 11/1971 | Kravitz |
| 3,623,475 A * | 11/1971 | Sanz et al. ................... 600/583 |
| 3,626,929 A | 12/1971 | Sanz et al. |
| 3,630,957 A | 12/1971 | Rey |
| D223,165 S | 3/1972 | Komendat |
| 3,723,064 A | 3/1973 | Liotta |
| 3,741,197 A | 6/1973 | Sanz et al. |
| 3,961,898 A | 6/1976 | Neeley et al. |
| 4,014,328 A | 3/1977 | Cluff et al. |
| 4,042,335 A | 8/1977 | Clement |

(Continued)

FOREIGN PATENT DOCUMENTS

| CA | 2 513 465 A1 | 8/2004 |
| DE | 199 22 413 A1 | 11/2000 |

(Continued)

OTHER PUBLICATIONS

European Examination Report mailed on Mar. 18, 2011, for EP Patent Application No. 06 815 329.5 filed on Sep. 26, 2006, five pages.

(Continued)

*Primary Examiner* — Rene Towa
*Assistant Examiner* — Emily Lloyd
(74) *Attorney, Agent, or Firm* — Morrison & Foerster LLP

(57) ABSTRACT

Arrangements are provided including a base having a bore disposed therein extending from a first surface of the base through a second surface of the base, a fluid transport tube having a first end, a second end opposite the first end, and a lumen having an inner diameter, at least the second end of the tube being received within the bore of the base, and at least one fluid transport enhancing groove having at least a first section disposed in the second surface of the base and in fluid communication with the bore.

33 Claims, 13 Drawing Sheets

(56) References Cited

U.S. PATENT DOCUMENTS

| | | | |
|---|---|---|---|
| 4,057,394 | A | 11/1977 | Genshaw |
| 4,109,655 | A | 8/1978 | Chacornac |
| 4,254,083 | A | 3/1981 | Columbus |
| 4,258,001 | A | 3/1981 | Pierce et al. |
| 4,260,257 | A | 4/1981 | Neeley et al. |
| 4,289,459 | A | 9/1981 | Neeley et al. |
| 4,321,397 | A | 3/1982 | Nix et al. |
| 4,350,762 | A | 9/1982 | DeLuca et al. |
| 4,394,512 | A | 7/1983 | Batz |
| 4,414,975 | A | 11/1983 | Ryder et al. |
| 4,416,279 | A | 11/1983 | Lindner et al. |
| 4,418,037 | A | 11/1983 | Katsuyama et al. |
| 4,422,941 | A | 12/1983 | Vaughan, Jr. et al. |
| 4,429,700 | A | 2/1984 | Thees et al. |
| 4,627,445 | A | 12/1986 | Garcia et al. |
| 4,637,403 | A * | 1/1987 | Garcia et al. ............ 600/583 |
| 4,637,406 | A | 1/1987 | Guinn et al. |
| 4,653,513 | A | 3/1987 | Dombrowski |
| 4,661,319 | A | 4/1987 | Lape |
| 4,702,261 | A | 10/1987 | Cornell et al. |
| 4,711,250 | A | 12/1987 | Gilbaugh, Jr. et al. |
| 4,737,458 | A | 4/1988 | Batz et al. |
| 4,767,415 | A * | 8/1988 | Duffy ..................... 604/232 |
| 4,774,192 | A | 9/1988 | Terminiello et al. |
| 4,790,979 | A | 12/1988 | Terminiello et al. |
| 4,794,926 | A | 1/1989 | Munsch et al. |
| 4,815,843 | A | 3/1989 | Tiefenthaler et al. |
| 4,829,470 | A | 5/1989 | Wang |
| 4,846,785 | A | 7/1989 | Cassou et al. |
| 4,887,306 | A | 12/1989 | Hwang et al. |
| 4,920,977 | A | 5/1990 | Haynes |
| 4,930,525 | A | 6/1990 | Palestrant |
| 4,935,346 | A | 6/1990 | Phillips |
| 4,953,552 | A | 9/1990 | De Marzo |
| 4,966,646 | A | 10/1990 | Zdeblick |
| 4,995,402 | A | 2/1991 | Smith |
| 5,029,583 | A | 7/1991 | Meserol |
| 5,049,487 | A | 9/1991 | Phillips et al. |
| 5,050,617 | A | 9/1991 | Columbus et al. |
| 5,059,394 | A | 10/1991 | Phillips et al. |
| 5,077,199 | A | 12/1991 | Basagni et al. |
| 5,094,943 | A | 3/1992 | Siedel et al. |
| 5,116,759 | A | 5/1992 | Klainer et al. |
| 5,131,404 | A | 7/1992 | Neeley et al. |
| 5,141,868 | A | 8/1992 | Shanks et al. |
| 5,145,565 | A | 9/1992 | Kater et al. |
| 5,146,437 | A | 9/1992 | Boucheron |
| 5,153,416 | A | 10/1992 | Neeley |
| 5,164,575 | A | 11/1992 | Neeley et al. |
| 5,166,498 | A | 11/1992 | Neeley |
| 5,174,291 | A | 12/1992 | Schoonen et al. |
| 5,176,632 | A | 1/1993 | Bernardi |
| 5,179,005 | A | 1/1993 | Phillips et al. |
| 5,183,741 | A | 2/1993 | Arai et al. |
| 5,196,302 | A | 3/1993 | Kidwell |
| 5,208,163 | A | 5/1993 | Charlton et al. |
| 5,213,966 | A | 5/1993 | Vuorinen et al. |
| 5,217,480 | A | 6/1993 | Habar et al. |
| 5,218,966 | A | 6/1993 | Yamasawa |
| 5,223,219 | A | 6/1993 | Subramanian et al. |
| 5,234,818 | A | 8/1993 | Zimmermann et al. |
| 5,241,969 | A | 9/1993 | Carson et al. |
| 5,251,126 | A | 10/1993 | Kahn et al. |
| D341,848 | S | 11/1993 | Bigelow et al. |
| 5,275,159 | A | 1/1994 | Griebel |
| 5,278,079 | A | 1/1994 | Gubinski et al. |
| 5,288,646 | A | 2/1994 | Lundsgaard et al. |
| 5,299,571 | A | 4/1994 | Mastrototaro |
| 5,301,686 | A | 4/1994 | Newman |
| 5,302,513 | A | 4/1994 | Mike et al. |
| 5,304,468 | A | 4/1994 | Phillips et al. |
| 5,306,623 | A | 4/1994 | Kiser et al. |
| 5,308,767 | A | 5/1994 | Terashima |
| 5,320,607 | A | 6/1994 | Ishibashi |
| 5,354,537 | A | 10/1994 | Moreno |
| 5,360,595 | A | 11/1994 | Bell et al. |
| 5,368,047 | A | 11/1994 | Suzuki et al. |
| 5,383,512 | A | 1/1995 | Jarvis |
| 5,390,671 | A | 2/1995 | Lord et al. |
| 5,399,316 | A | 3/1995 | Yamada |
| 5,401,110 | A | 3/1995 | Neeley |
| 5,402,798 | A | 4/1995 | Swierczek et al. |
| 5,441,513 | A | 8/1995 | Roth |
| 5,451,350 | A | 9/1995 | Macho et al. |
| 5,458,140 | A | 10/1995 | Eppstein et al. |
| 5,460,777 | A | 10/1995 | Kitajima et al. |
| 5,460,968 | A | 10/1995 | Yoshida et al. |
| 5,482,473 | A | 1/1996 | Lord et al. |
| 5,506,200 | A | 4/1996 | Hirschkoff et al. |
| 5,507,288 | A | 4/1996 | Böcker et al. |
| 5,508,200 | A | 4/1996 | Tiffany et al. |
| 5,510,266 | A | 4/1996 | Bonner et al. |
| 5,514,152 | A | 5/1996 | Smith |
| 5,568,806 | A | 10/1996 | Cheney, II et al. |
| 5,569,287 | A | 10/1996 | Tezuka et al. |
| 5,575,403 | A | 11/1996 | Charlton et al. |
| 5,577,499 | A | 11/1996 | Teves |
| 5,582,184 | A | 12/1996 | Erickson et al. |
| 5,586,553 | A | 12/1996 | Halili et al. |
| 5,591,139 | A | 1/1997 | Lin et al. |
| 5,611,809 | A | 3/1997 | Marshall et al. |
| 5,624,458 | A | 4/1997 | Lipscher |
| 5,630,986 | A | 5/1997 | Charlton et al. |
| 5,632,410 | A | 5/1997 | Moulton et al. |
| 5,636,632 | A | 6/1997 | Bommannan et al. |
| 5,647,851 | A | 7/1997 | Pokras |
| 5,658,515 | A | 8/1997 | Lee et al. |
| 5,660,791 | A | 8/1997 | Brenneman et al. |
| 5,676,850 | A | 10/1997 | Reed et al. |
| 5,680,858 | A | 10/1997 | Hansen et al. |
| 5,681,484 | A | 10/1997 | Zanzucchi et al. |
| 5,682,233 | A | 10/1997 | Brinda |
| 5,697,901 | A | 12/1997 | Eriksson |
| 5,701,181 | A | 12/1997 | Boiarski et al. |
| 5,701,910 | A | 12/1997 | Powles et al. |
| 5,705,018 | A | 1/1998 | Hartley |
| 5,708,787 | A | 1/1998 | Nakano et al. |
| 5,715,417 | A | 2/1998 | Gardien et al. |
| 5,730,753 | A | 3/1998 | Morita |
| 5,735,273 | A | 4/1998 | Kurnik et al. |
| 5,736,103 | A | 4/1998 | Pugh |
| 5,741,211 | A | 4/1998 | Renirie et al. |
| 5,746,217 | A | 5/1998 | Erickson et al. |
| 5,746,720 | A | 5/1998 | Stouder, Jr. |
| 5,757,666 | A | 5/1998 | Schreiber et al. |
| 5,759,364 | A | 6/1998 | Charlton et al. |
| 5,766,066 | A | 6/1998 | Ranniger |
| 5,771,890 | A | 6/1998 | Tamada |
| 5,797,693 | A | 8/1998 | Jaeger |
| 5,801,057 | A | 9/1998 | Smart et al. |
| 5,807,375 | A | 9/1998 | Gross et al. |
| 5,820,570 | A | 10/1998 | Erickson et al. |
| 5,827,183 | A | 10/1998 | Kurnik et al. |
| 5,840,020 | A | 11/1998 | Heinonen et al. |
| 5,841,126 | A | 11/1998 | Fossum et al. |
| 5,843,692 | A | 12/1998 | Phillips et al. |
| 5,846,837 | A | 12/1998 | Thym et al. |
| 5,854,074 | A | 12/1998 | Charlton et al. |
| D403,975 | S | 1/1999 | Douglas et al. |
| 5,855,801 | A | 1/1999 | Lin et al. |
| 5,856,195 | A | 1/1999 | Charlton et al. |
| 5,858,194 | A | 1/1999 | Bell |
| 5,866,281 | A | 2/1999 | Guckel et al. |
| 5,871,494 | A | 2/1999 | Simons et al. |
| 5,879,310 | A | 3/1999 | Sopp et al. |
| 5,879,326 | A | 3/1999 | Godshall et al. |
| 5,879,367 | A | 3/1999 | Latterell et al. |
| 5,891,053 | A | 4/1999 | Sesekura |
| 5,893,870 | A | 4/1999 | Talen et al. |
| 5,911,711 | A | 6/1999 | Pelkey |
| 5,911,737 | A | 6/1999 | Lee et al. |
| 5,912,139 | A | 6/1999 | Iwata et al. |
| 5,925,021 | A | 7/1999 | Castellano et al. |
| 5,928,207 | A | 7/1999 | Pisano et al. |

(56) References Cited

U.S. PATENT DOCUMENTS

| | | |
|---|---|---|
| 5,930,873 A | 8/1999 | Wyser |
| 5,938,679 A | 8/1999 | Freeman et al. |
| 5,945,678 A | 8/1999 | Yanagisawa |
| 5,951,492 A * | 9/1999 | Douglas et al. ............... 600/583 |
| 5,951,493 A | 9/1999 | Douglas et al. |
| 5,954,685 A | 9/1999 | Tierney |
| 5,962,215 A | 10/1999 | Douglas et al. |
| 5,968,760 A | 10/1999 | Phillips et al. |
| 5,968,765 A | 10/1999 | Grage et al. |
| 5,971,941 A | 10/1999 | Simons et al. |
| 5,972,294 A | 10/1999 | Smith et al. |
| 5,986,754 A | 11/1999 | Harding |
| 5,989,409 A | 11/1999 | Kurnik et al. |
| 5,993,189 A | 11/1999 | Mueller et al. |
| 6,001,067 A | 12/1999 | Shults et al. |
| 6,005,545 A | 12/1999 | Nishida et al. |
| 6,010,463 A | 1/2000 | Lauks et al. |
| 6,010,519 A | 1/2000 | Mawhirt et al. |
| 6,014,135 A | 1/2000 | Fernandes |
| 6,014,577 A | 1/2000 | Henning et al. |
| 6,023,629 A | 2/2000 | Tamada |
| 6,027,459 A | 2/2000 | Shain et al. |
| 6,030,827 A | 2/2000 | Davis et al. |
| 6,032,059 A | 2/2000 | Henning et al. |
| 6,036,924 A | 3/2000 | Simons et al. |
| 6,041,253 A | 3/2000 | Kost et al. |
| 6,050,988 A | 4/2000 | Zuck |
| 6,056,701 A | 5/2000 | Duchon et al. |
| 6,056,734 A | 5/2000 | Jacobsen et al. |
| 6,058,321 A | 5/2000 | Swayze et al. |
| 6,059,815 A | 5/2000 | Lee et al. |
| 6,061,128 A | 5/2000 | Zweig et al. |
| 6,063,039 A | 5/2000 | Cunningham et al. |
| 6,071,294 A | 6/2000 | Simons et al. |
| 6,077,660 A | 6/2000 | Wong et al. |
| 6,080,116 A | 6/2000 | Erickson et al. |
| 6,083,196 A | 7/2000 | Trautman et al. |
| 6,086,544 A | 7/2000 | Hibner et al. |
| 6,090,790 A | 7/2000 | Eriksson |
| 6,091,975 A | 7/2000 | Daddona et al. |
| 6,093,156 A | 7/2000 | Cunningham et al. |
| 6,097,831 A | 8/2000 | Wieck et al. |
| 6,099,484 A | 8/2000 | Douglas et al. |
| 6,100,107 A | 8/2000 | Lei et al. |
| 6,102,933 A | 8/2000 | Lee et al. |
| 6,103,033 A | 8/2000 | Say et al. |
| 6,103,197 A | 8/2000 | Werner |
| 6,106,751 A | 8/2000 | Talbot et al. |
| 6,118,126 A | 9/2000 | Zanzucchi |
| 6,120,676 A | 9/2000 | Heller et al. |
| 6,123,861 A | 9/2000 | Santini, Jr. et al. |
| 6,126,899 A | 10/2000 | Woudenberg et al. |
| 6,132,449 A | 10/2000 | Lum et al. |
| 6,139,562 A | 10/2000 | Mauze et al. |
| 6,142,939 A | 11/2000 | Eppstein et al. |
| 6,152,942 A | 11/2000 | Brenneman et al. |
| 6,162,639 A | 12/2000 | Douglas |
| 6,175,752 B1 | 1/2001 | Say et al. |
| 6,176,865 B1 | 1/2001 | Mauze et al. |
| 6,183,434 B1 * | 2/2001 | Eppstein ..................... 600/583 |
| 6,183,489 B1 | 2/2001 | Douglas et al. |
| 6,187,210 B1 | 2/2001 | Lebouiz et al. |
| 6,192,891 B1 | 2/2001 | Gravel et al. |
| 6,200,296 B1 | 3/2001 | Dibiasi et al. |
| 6,206,841 B1 | 3/2001 | Cunningham et al. |
| 6,214,626 B1 | 4/2001 | Meller et al. |
| 6,219,574 B1 | 4/2001 | Cormier et al. |
| 6,228,100 B1 | 5/2001 | Schraga |
| 6,230,051 B1 | 5/2001 | Cormier et al. |
| 6,231,531 B1 | 5/2001 | Lum et al. |
| 6,241,862 B1 | 6/2001 | McAleer et al. |
| 6,242,207 B1 | 6/2001 | Douglas et al. |
| 6,245,215 B1 | 6/2001 | Douglas et al. |
| 6,251,083 B1 | 6/2001 | Yum et al. |
| 6,251,260 B1 | 6/2001 | Heller et al. |
| 6,254,586 B1 | 7/2001 | Mann et al. |
| 6,255,061 B1 | 7/2001 | Mori et al. |
| 6,256,533 B1 | 7/2001 | Yuzhakov et al. |
| 6,268,162 B1 | 7/2001 | Phillips et al. |
| 6,271,045 B1 | 8/2001 | Douglas et al. |
| 6,272,364 B1 | 8/2001 | Kurnik |
| 6,283,926 B1 | 9/2001 | Cunningham et al. |
| 6,289,230 B1 | 9/2001 | Chaiken et al. |
| 6,298,254 B2 | 10/2001 | Tamada |
| 6,299,578 B1 | 10/2001 | Kurnik et al. |
| 6,309,351 B1 | 10/2001 | Kurnik et al. |
| D450,711 S | 11/2001 | Istvan et al. |
| 6,312,612 B1 | 11/2001 | Sherman et al. |
| 6,312,888 B1 | 11/2001 | Wong et al. |
| 6,322,808 B1 | 11/2001 | Trautman et al. |
| 6,329,161 B1 | 12/2001 | Heller et al. |
| 6,331,266 B1 | 12/2001 | Powell et al. |
| 6,332,871 B1 | 12/2001 | Douglas et al. |
| 6,334,856 B1 | 1/2002 | Allen et al. |
| 6,350,273 B1 | 2/2002 | Minagawa et al. |
| 6,352,514 B1 | 3/2002 | Douglas et al. |
| 6,356,776 B1 | 3/2002 | Berner et al. |
| 6,358,265 B1 | 3/2002 | Thorne, Jr. et al. |
| 6,364,890 B1 | 4/2002 | Lum et al. |
| 6,375,626 B1 * | 4/2002 | Allen et al. .................... 600/584 |
| 6,375,627 B1 | 4/2002 | Mauze et al. |
| 6,379,969 B1 | 4/2002 | Mauze et al. |
| 6,391,005 B1 | 5/2002 | Lum et al. |
| 6,409,679 B2 | 6/2002 | Pyo |
| 6,428,664 B1 | 8/2002 | Bhular et al. |
| 6,449,608 B1 | 9/2002 | Morita et al. |
| 6,455,324 B1 | 9/2002 | Douglas |
| 6,500,134 B1 | 12/2002 | Cassone |
| 6,520,973 B1 | 2/2003 | McGarry |
| 6,530,892 B1 | 3/2003 | Kelly |
| 6,537,243 B1 | 3/2003 | Henning et al. |
| 6,540,675 B2 | 4/2003 | Aceti et al. |
| 6,544,475 B1 | 4/2003 | Douglas et al. |
| 6,555,061 B1 | 4/2003 | Leong et al. |
| 6,558,624 B1 | 5/2003 | Lemmon et al. |
| 6,579,690 B1 | 6/2003 | Bonnecaze et al. |
| 6,602,205 B1 | 8/2003 | Erickson et al. |
| 6,612,111 B1 | 9/2003 | Hodges et al. |
| 6,616,616 B2 | 9/2003 | Fritz et al. |
| 6,626,874 B1 | 9/2003 | Duchamp |
| 6,656,167 B2 | 12/2003 | Numao et al. |
| 6,679,852 B1 | 1/2004 | Schmelzeisen-Redeker et al. |
| 6,706,000 B2 | 3/2004 | Perez et al. |
| 6,706,049 B2 | 3/2004 | Moerman |
| 6,706,159 B2 | 3/2004 | Moerman et al. |
| 6,740,800 B1 | 5/2004 | Cunningham |
| 6,748,275 B2 | 6/2004 | Lattner et al. |
| 6,753,187 B2 | 6/2004 | Cizdziel et al. |
| 6,766,817 B2 | 7/2004 | da Silva |
| 6,793,633 B2 | 9/2004 | Douglas et al. |
| 6,830,669 B2 | 12/2004 | Miyazaki et al. |
| 6,836,678 B2 | 12/2004 | Tu |
| 6,837,858 B2 | 1/2005 | Cunningham et al. |
| 6,847,451 B2 | 1/2005 | Pugh |
| 6,918,404 B2 | 7/2005 | Da Silva |
| 6,919,960 B2 | 7/2005 | Hansen et al. |
| 6,923,764 B2 | 8/2005 | Aceti et al. |
| 6,936,476 B1 | 8/2005 | Anderson et al. |
| 6,988,996 B2 | 1/2006 | Roe et al. |
| 7,004,928 B2 | 2/2006 | Aceti et al. |
| 7,011,630 B2 | 3/2006 | Desai et al. |
| 7,025,774 B2 | 4/2006 | Freeman et al. |
| 7,066,586 B2 | 6/2006 | Da Silva |
| 7,066,890 B1 | 6/2006 | Lam et al. |
| 7,141,058 B2 | 11/2006 | Briggs et al. |
| 7,156,809 B2 | 1/2007 | Quy |
| 7,192,061 B2 | 3/2007 | Martin |
| D540,343 S | 4/2007 | Cummins |
| 7,223,365 B2 | 5/2007 | Von Der Goltz |
| 7,225,008 B1 | 5/2007 | Ward et al. |
| 7,226,461 B2 | 6/2007 | Boecker et al. |
| D551,243 S | 9/2007 | Young |
| 7,270,970 B2 | 9/2007 | Anderson et al. |
| 7,297,151 B2 | 11/2007 | Boecker et al. |

(56) References Cited

U.S. PATENT DOCUMENTS

| | | |
|---|---|---|
| 7,343,188 B2 | 3/2008 | Sohrab |
| 7,344,507 B2 | 3/2008 | Briggs et al. |
| 7,427,377 B2 | 9/2008 | Zanzucchi et al. |
| D599,373 S | 9/2009 | Kobayashi et al. |
| D601,578 S | 10/2009 | Poulet et al. |
| 7,682,318 B2 | 3/2010 | Alden et al. |
| 7,803,123 B2 | 9/2010 | Perez et al. |
| 7,887,494 B2 | 2/2011 | Emery et al. |
| D642,191 S | 7/2011 | Barnett et al. |
| 2001/0001034 A1 | 5/2001 | Douglas |
| 2001/0027328 A1 | 10/2001 | Lum et al. |
| 2001/0053891 A1 | 12/2001 | Ackley |
| 2002/0002326 A1 | 1/2002 | Causey, III et al. |
| 2002/0002344 A1 | 1/2002 | Douglas et al. |
| 2002/0004640 A1 | 1/2002 | Conn et al. |
| 2002/0006355 A1 | 1/2002 | Whitson |
| 2002/0016568 A1 | 2/2002 | Lebel et al. |
| 2002/0020688 A1 | 2/2002 | Sherman et al. |
| 2002/0023852 A1 | 2/2002 | Mcivor et al. |
| 2002/0042594 A1 | 4/2002 | Lum et al. |
| 2002/0052618 A1 | 5/2002 | Haar et al. |
| 2002/0087056 A1 | 7/2002 | Aceti et al. |
| 2002/0136667 A1 | 9/2002 | Subramanian et al. |
| 2002/0137998 A1 | 9/2002 | Smart et al. |
| 2002/0160520 A1 | 10/2002 | Orloff et al. |
| 2002/0168290 A1 | 11/2002 | Yuzhakov et al. |
| 2002/0169394 A1 | 11/2002 | Eppstein et al. |
| 2002/0169411 A1 | 11/2002 | Sherman et al. |
| 2002/0177761 A1 | 11/2002 | Orloff et al. |
| 2002/0183102 A1 | 12/2002 | Withers et al. |
| 2002/0188223 A1 | 12/2002 | Perez et al. |
| 2002/0198444 A1 | 12/2002 | Uchigaki et al. |
| 2003/0012693 A1 | 1/2003 | Otillar et al. |
| 2003/0028087 A1 | 2/2003 | Yuzhakov et al. |
| 2003/0028125 A1 | 2/2003 | Yuzhakov et al. |
| 2003/0039587 A1* | 2/2003 | Niermann ............. 422/100 |
| 2003/0083685 A1 | 5/2003 | Freeman et al. |
| 2003/0083686 A1 | 5/2003 | Freeman et al. |
| 2003/0116596 A1 | 6/2003 | Terasawa |
| 2003/0135166 A1 | 7/2003 | Gonnelli |
| 2003/0135333 A1 | 7/2003 | Aceti |
| 2003/0153844 A1 | 8/2003 | Smith et al. |
| 2003/0153900 A1 | 8/2003 | Aceti et al. |
| 2003/0175987 A1 | 9/2003 | Verdonk et al. |
| 2003/0206302 A1 | 11/2003 | Pugh |
| 2003/0207441 A1 | 11/2003 | Eyster et al. |
| 2003/0208113 A1 | 11/2003 | Mault et al. |
| 2003/0211619 A1 | 11/2003 | Olson et al. |
| 2003/0212344 A1 | 11/2003 | Yuzhakov et al. |
| 2003/0212347 A1 | 11/2003 | Sohrab |
| 2004/0010207 A1 | 1/2004 | Flaherty et al. |
| 2004/0030353 A1 | 2/2004 | Schmelzeisen-redeker et al. |
| 2004/0049219 A1 | 3/2004 | Briggs et al. |
| 2004/0059256 A1 | 3/2004 | Perez |
| 2004/0073140 A1 | 4/2004 | Douglas |
| 2004/0092842 A1 | 5/2004 | Boecker et al. |
| 2004/0092995 A1 | 5/2004 | Boecker et al. |
| 2004/0096959 A1* | 5/2004 | Stiene et al. ............. 435/287.2 |
| 2004/0098009 A1 | 5/2004 | Boecker et al. |
| 2004/0102803 A1 | 5/2004 | Boecker et al. |
| 2004/0122339 A1* | 6/2004 | Roe ............. 600/583 |
| 2004/0132167 A1 | 7/2004 | Rule et al. |
| 2004/0138588 A1 | 7/2004 | Saikley et al. |
| 2004/0155084 A1 | 8/2004 | Brown |
| 2004/0178218 A1 | 9/2004 | Schomakers et al. |
| 2004/0186394 A1* | 9/2004 | Roe et al. ............. 600/583 |
| 2004/0191119 A1* | 9/2004 | Zanzucchi et al. ............. 422/58 |
| 2004/0202576 A1 | 10/2004 | Aceti et al. |
| 2004/0236251 A1 | 11/2004 | Roe et al. |
| 2004/0238675 A1 | 12/2004 | Banaszkiewicz et al. |
| 2005/0010134 A1 | 1/2005 | Douglas et al. |
| 2005/0015020 A1 | 1/2005 | LeVaughn et al. |
| 2005/0096686 A1 | 5/2005 | Allen |
| 2005/0106713 A1 | 5/2005 | Phan et al. |
| 2005/0159678 A1 | 7/2005 | Taniike et al. |
| 2005/0178218 A1 | 8/2005 | Montagu |
| 2005/0187532 A1 | 8/2005 | Thurau et al. |
| 2005/0202567 A1 | 9/2005 | Zanzucchi et al. |
| 2005/0202733 A1 | 9/2005 | Yoshimura et al. |
| 2005/0215872 A1 | 9/2005 | Berner et al. |
| 2005/0215923 A1 | 9/2005 | Wiegel |
| 2005/0245844 A1 | 11/2005 | Mace et al. |
| 2005/0277972 A1 | 12/2005 | Wong et al. |
| 2006/0008389 A1 | 1/2006 | Sacherer et al. |
| 2006/0036134 A1 | 2/2006 | Tarassenko et al. |
| 2006/0117616 A1 | 6/2006 | Jones et al. |
| 2006/0135873 A1 | 6/2006 | Karo et al. |
| 2006/0155317 A1 | 7/2006 | List |
| 2006/0178600 A1 | 8/2006 | Kennedy et al. |
| 2006/0189908 A1 | 8/2006 | Kennedy |
| 2006/0204399 A1 | 9/2006 | Freeman et al. |
| 2006/0229533 A1 | 10/2006 | Hoenes et al. |
| 2006/0241517 A1 | 10/2006 | Fowler et al. |
| 2006/0257993 A1 | 11/2006 | Mcdevitt et al. |
| 2006/0259102 A1 | 11/2006 | Slatkine |
| 2006/0281187 A1 | 12/2006 | Emery et al. |
| 2007/0017824 A1 | 1/2007 | Rippeth et al. |
| 2007/0078313 A1 | 4/2007 | Emery et al. |
| 2007/0078358 A1 | 4/2007 | Escutia et al. |
| 2007/0083131 A1 | 4/2007 | Escutia et al. |
| 2007/0179404 A1 | 8/2007 | Escutia et al. |
| 2007/0179405 A1 | 8/2007 | Emery et al. |
| 2007/0255181 A1 | 11/2007 | Alvarez-icaza et al. |
| 2007/0255302 A1 | 11/2007 | Koeppel et al. |
| 2008/0046831 A1 | 2/2008 | Imai et al. |
| 2008/0077048 A1 | 3/2008 | Escutia et al. |
| 2008/0194934 A1 | 8/2008 | Ray et al. |
| 2009/0156923 A1 | 6/2009 | Power et al. |
| 2010/0021948 A1 | 1/2010 | Lipman et al. |
| 2010/0095229 A1 | 4/2010 | Dixon et al. |
| 2010/0185120 A1 | 7/2010 | Sacherer et al. |
| 2012/0166090 A1 | 6/2012 | Lipman et al. |

FOREIGN PATENT DOCUMENTS

| | | |
|---|---|---|
| DE | 103 02-501 A1 | 8/2004 |
| EP | 0 396-016 A2 | 11/1990 |
| EP | 0 396-016 A3 | 11/1990 |
| EP | 0 255-338 A2 | 2/1998 |
| EP | 1 266-607 A2 | 12/2002 |
| EP | 1 266-607 A3 | 12/2002 |
| EP | 1 360-934 A1 | 11/2003 |
| EP | 1 360-934 B1 | 11/2003 |
| EP | 1 486 766 A1 | 12/2004 |
| EP | 1 529-489 A1 | 5/2005 |
| EP | 1 529-489 B1 | 5/2005 |
| EP | 1 769-735 A1 | 4/2007 |
| EP | 1 769 735 A1 | 4/2007 |
| JP | 63-305841 A | 12/1988 |
| JP | 3-63570 A | 3/1991 |
| JP | 03093189 A | 4/1991 |
| JP | 7-67861 A | 3/1995 |
| JP | 7-213925 A | 8/1995 |
| JP | 9-168530 A | 6/1997 |
| JP | 9-313465 A | 9/1997 |
| JP | 9-266889 A | 10/1997 |
| JP | 9-294737 A | 11/1997 |
| JP | 10-024028 A | 1/1998 |
| JP | 10-318970 A | 12/1998 |
| JP | 2000126161 A | 5/2000 |
| JP | 2000-168754 A | 6/2000 |
| JP | 2000-254111 A | 9/2000 |
| JP | 2001-159618 A | 6/2001 |
| JP | 2001-305096 A | 10/2001 |
| JP | 2001-330581 A | 11/2001 |
| JP | 2002-502045 A | 1/2002 |
| JP | 2002-514453 A | 5/2002 |
| JP | 2003-180417 A | 7/2003 |
| JP | 2004-000598 A | 1/2004 |
| JP | 2004-500948 A | 1/2004 |
| JP | 2004-117339 A | 4/2004 |
| JP | 2004-522500 A | 7/2004 |
| JP | 2004-528936 A | 9/2004 |
| JP | 2005-503538 A | 2/2005 |

(56) References Cited

FOREIGN PATENT DOCUMENTS

| | | |
|---|---|---|
| JP | 2005-087613 A | 4/2005 |
| JP | 2006-512969 A | 4/2005 |
| JP | 2005-525149 A | 8/2005 |
| JP | 2005-237938 A | 9/2005 |
| JP | 2005-525846 A | 9/2005 |
| JP | 2005-527254 A | 9/2005 |
| JP | 2006-512974 A | 4/2006 |
| JP | 2006-516723 A | 7/2006 |
| JP | 2006-521555 A | 9/2006 |
| JP | 2006-527013 A | 11/2006 |
| JP | 2007-521031 A | 8/2007 |
| WO | WO-91/14212 A1 | 9/1991 |
| WO | WO-94/13203 A1 | 6/1994 |
| WO | WO-95/10223 A2 | 4/1995 |
| WO | WO-95/10223 A3 | 4/1995 |
| WO | WO-96/04857 A1 | 2/1996 |
| WO | WO-96/14026 A1 | 5/1996 |
| WO | WO-96/25088 A1 | 8/1996 |
| WO | WO-97/15227 A1 | 5/1997 |
| WO | WO-97/29847 A1 | 8/1997 |
| WO | WO-97/30344 A1 | 8/1997 |
| WO | WO-97/41421 A1 | 11/1997 |
| WO | WO-98/31275 A1 | 7/1998 |
| WO | WO-98/35225 A1 | 8/1998 |
| WO | WO-99/12008 A1 | 3/1999 |
| WO | WO-99/44508 A1 | 9/1999 |
| WO | WO-99/58051 A1 | 11/1999 |
| WO | WO-00/09184 A1 | 2/2000 |
| WO | WO-00/13573 A1 | 3/2000 |
| WO | WO-00/14269 A1 | 3/2000 |
| WO | WO-00/14535 A1 | 3/2000 |
| WO | WO-00/18449 A2 | 4/2000 |
| WO | WO-00/18449 A3 | 4/2000 |
| WO | WO-00/36400 A1 | 6/2000 |
| WO | WO-00/42422 A1 | 7/2000 |
| WO | WO-00/74763 A2 | 12/2000 |
| WO | WO-00/74763 A3 | 12/2000 |
| WO | WO-00/78208 A1 | 12/2000 |
| WO | WO-01/16575 A1 | 3/2001 |
| WO | WO-01/52727 A1 | 7/2001 |
| WO | WO-01/64105 A1 | 9/2001 |
| WO | WO-01/64105 C2 | 9/2001 |
| WO | WO-01/72220 A1 | 10/2001 |
| WO | WO-01/80728 A1 | 11/2001 |
| WO | WO-01/85233 A2 | 11/2001 |
| WO | WO-01/85233 A3 | 11/2001 |
| WO | WO-01/91634 A2 | 12/2001 |
| WO | WO-01/91634 A3 | 12/2001 |
| WO | WO-02/00101 A2 | 1/2002 |
| WO | WO-02/00101 A3 | 1/2002 |
| WO | WO-02/49507 A1 | 6/2002 |
| WO | WO-02/49509 A2 | 6/2002 |
| WO | WO-02/49509 A3 | 6/2002 |
| WO | WO-02/082052 A2 | 10/2002 |
| WO | WO-02/082052 A3 | 10/2002 |
| WO | WO-02/093144 A1 | 11/2002 |
| WO | WO-02/100251 A2 | 12/2002 |
| WO | WO-02/100251 A3 | 12/2002 |
| WO | WO-02/101359 A2 | 12/2002 |
| WO | WO-02/101359 A3 | 12/2002 |
| WO | WO-03/030984 A1 | 4/2003 |
| WO | WO-03/066128 A2 | 8/2003 |
| WO | WO-03/066128 A3 | 8/2003 |
| WO | WO-03/070099 A1 | 8/2003 |
| WO | WO-03/071940 A1 | 9/2003 |
| WO | WO-03/071940 C1 | 9/2003 |
| WO | WO-2004/062499 A1 | 7/2004 |
| WO | WO-2004/062500 A1 | 7/2004 |
| WO | WO-2004/062500 C1 | 7/2004 |
| WO | WO-2004/064636 A1 | 8/2004 |
| WO | WO-2005/006939 A2 | 1/2005 |
| WO | WO-2005/006939 A3 | 1/2005 |
| WO | WO-2005/009238 A1 | 2/2005 |
| WO | WO-2005/018709 A2 | 3/2005 |
| WO | WO-2005/018709 A3 | 3/2005 |
| WO | WO-2005/084546 A2 | 9/2005 |
| WO | WO-2005/084546 A3 | 9/2005 |
| WO | WO-2005/085995 A1 | 9/2005 |
| WO | WO-2005/084546 A2 | 4/2007 |
| WO | WO-2005/084546 A3 | 4/2007 |
| WO | WO-2007/041063 A2 | 4/2007 |
| WO | WO-2007/041063 A3 | 4/2007 |
| WO | WO-2007/041244 A2 | 4/2007 |
| WO | WO-2007/041244 A3 | 4/2007 |
| WO | WO-2007/041287 A2 | 4/2007 |
| WO | WO-2007/041287 A3 | 4/2007 |
| WO | WO-2007/041355 A2 | 4/2007 |
| WO | WO-2007/041355 A3 | 4/2007 |

OTHER PUBLICATIONS

ADA Consensus Development Panel. (Jan.-Feb. 1987). "Consensus Statement on Self-Monitoring of Blood Glucose," *Diabetes Care* 10(1):95-99.

ADA (Jan. 1994). "Self-Monitoring of Blood Glucose," Consensus Statement *Diabetes Care* 17(1):81-86.

Anonymous. (Sep. 30, 1993). "The Effect of Intensive Treatment of Diabetes on the Development and Progression of Long-Term Complications in Insulin-Dependent Diabetes Mellitus." *The New England Journal of Medicine* 329(14):977-986.

Anonymous. (Jun. 23, 1998). Taking the "Ouch" Out of Needles: Arrays of "Microneedles" Offer New Techniques for Drug Delivery, *Science Daily*, located at <http:www.sciencedaily.com/releases/1998/06/980623045850.htm>, last visited Jan. 14, 2014, 3 pages.

Beregszàszi, M. et al. (Jul. 1997). "Nocturnal Hypoglycemia in Children and Adolescents with Insulin-Dependent Diabetes Mellitus: Prevalence and Risk Factors," *J. Pediatrics* 131(1 Pt. 1):27-33.

Chase, H.P. et al. (Feb. 2001). "Continuous Subcutaneous Glucose Monitoring in Children with Type 1 Diabetes," *Pediatrics* 107(2):222-226.

Clarke, W.L. et al. (Sep.-Oct. 1987). "Evaluating Clinical Accuracy of Systems for Self-Monitoring of Blood Glucose," *Diabetes Care* 10(5):622-628.

Cox, D.J. et al. (Jun. 1997). "Understanding Error Grid Analysis," *Diabetes Care* 20(6):911-912.

D'Arrigo, T.D. (Mar. 2000). "GlucoWatch Monitor Poised for Approval," *Diabetes Forecast*, 53(3):43-44.

European Examination Report mailed on Jul. 19, 2012, for EP Patent Application No. 06 815 329.5 filed on Sep. 26, 2006, five pages.

International Search Report mailed on Aug. 20, 2007 for PCT Application No. PCT/US2006/37245, filed on Sep. 26, 2006, 1 page.

Johnson, R.N. et al. (Jan. 1998). "Accuracy of Devices Used for Self-Monitoring of Blood Glucose," *Annals of Clinical Biochemistry* 35(1):68-74.

Johnson, R.N. et al. (Jan. 1999). "Analytical Error of Home Glucose Monitors: A Comparison of 18 Systems," *Annals of Clinical Biochemistry* 36(1):72-79.

Johnson, R.N. et al. (2001). "Error Detection and Measurement in Glucose Monitors," *Clinica Chimica Acta* 307:61-67.

Lee, S-C. (Jun. 1999). "Light Scattering by Closely Spaced Parallel Cylinders Embedded in a Finite Dielectric Slab," *Journal of the Optical Society of America A* 16(6):1350-1361.

McNichols, R.J. et al. (Jan. 2000). "Optical Glucose Sensing in Biological Fluids: An Overview," *Journal of Biomedical Optics*, 5(1):5-16.

Medline Plus. (Jun. 17, 2008). , Medical Encyclopedia, Monitor Blood Glucose-Series: Part 1-4, 6 pages.

Pfohl, M. et al. (2000). "Spot Glucose Measurement in Epidermal Interstitial Fluid—An Alternative to Capillary Blood Glucose Estimation," *Experimental and Clinical Endocrinology & Diabetes* 108(1):1-4.

Princen, H.M. (May 1969). "Capillary Phenomena in Assemblies of Parallel Cylinders, I. Capillary Rise Between Two Cylinders," *Journal of Colloid and Interface Science* 30(1):69-75.

Princen, H.M. (Jul. 1969). "Capillary Phenomena in Assemblies of Parallel Cylinders, II. Capillary Rise in Systems with More Than Two Cylinders," *Journal of Colloid and Interface Science* 30(3):359-371.

(56) References Cited

OTHER PUBLICATIONS

Rebrin, K. et al. (Sep. 1999). "Subcutaneous Glucose Predicts Plasma Glucose Independent of Insulin: Implications for Continuous Monitoring," *American Journal of Physiology* 277(3):E561-E571.

Trinder, P. (1969). "Determination of Glucose in Blood Using Glucose Oxidase with an Alternate Oxygen Acceptor," *Annals of Clinical Biochemistry* 6:24-28.

Written Opinion mailed on Aug. 20, 2007 for PCT Application No. PCT/US2006/37245, filed on Sep. 26, 2006, 7 pages.

Collison, M.E. et al. (Sep. 1999). "Analytical Characterization of Electrochemical Biosensor Test Strips for Measurement of Glucose in Low-Volume Interstitial Fluid Samples," *Clinical Chemistry* 45(9):1665-1673.

Feldman, B. et al. (2000). "FreeStyle™: A Small-Volume Electrochemical Glucose Sensor for Home Blood Glucose Testing," *Diabetes Technology and Therapeutics*, 2(2):221-229.

Kumetrix, Inc. (Dec. 1999). "Painless Blood Glucose Monitoring, Courtesy of the Mosquito," *Start-Up* pp. 27-28.

Mahler, R.J. et al. (1999). "Clinical Review 102, Type 2 Diabetes Melitus: Update on Diagnosis Pathophysiology, and Treatment," *The Journal of Clinical Endocrinology and Metabolism* 84(4):1165-1171.

McGarraugh, G. et al. (2001). "Physiological Influences on Off-Finger Glucose Testing," *Diabetes Technology & Therapeutics* 3(3):367-376.

Neeley, W.E. et al. (1981). "An Instrument for Digital Matrix Photometry," *Clinical Chemistry* 27(10):1665-1668.

Neeley, W.E. (1983). "Reflectance Digital Matrix Photometry," *Clinical Chemistry* 29(6):1038-1041.

Neeley, W.E. (1983). "Multilayer Film Analysis for Glucose in 1-µL Samples of Plasma," *Clinical Chemistry* 29(12):2103-2105.

Neeley, W.E. (1988). "A Reflectance Photometer with a Square Photodiode Array Detector for Use on Multilayer Dry-Film Slides," *Clinical Chemistry* 34(11):2367-2370.

Otto, E. et al. (2000). "An Intelligent Diabetes Software Prototype: Predicting Blood Glucose Levels and Recommending Regimen Changes," *Diabetes Technology and Therapeutics* 2(4):569-576.

Smart, W.H. et al. (2000). "The Use of Silicon Microfabrication Technology in Painless Glucose Monitoring, "*Diabetes Technology & Therapeutics* 2(4):549-559.

Svedman, C. et al. (Apr. 1999). "Skin Mini-Erosion Technique for Monitoring Metabolites in Interstitial Fluid: Its Feasibility Demonstrated by OGTT Results in Diabetic and Non-Diabetic Subjects," *Scand. J. Clin. Lab. Invest.* 59(2):115-123.

Yum, S. I. et al. (Nov. 1, 1999). "Capillary Blood Sampling for Self-Monitoring of Blood Glucose," *Diabetes Technology & Therapeutics*, 1(1):29-37.

\* cited by examiner

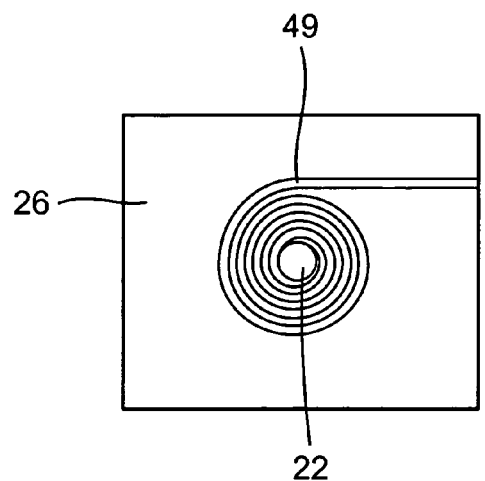
FIG. 17
FIG. 18
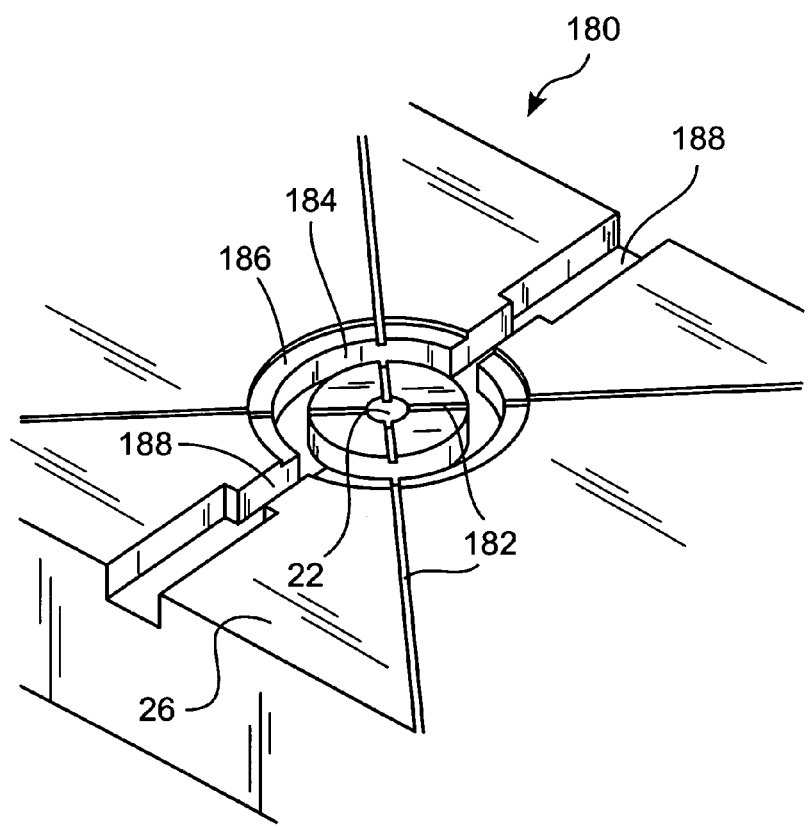

DEVICES AND METHODS FOR FACILITATING FLUID TRANSPORT

FIELD OF THE INVENTION

The presented invention is directed to devices, arrangements and associated methods for effectively transporting fluids, for example, samples of body fluids.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

According to the American Diabetes Association, diabetes is the fifth-deadliest disease in the United States and kills more than 213,000 people a year, the total economic cost of diabetes in 2002 was estimated at over $132 billion dollars, and the risk of developing type I juvenile diabetes is higher than virtually all other chronic childhood diseases.

In certain medical treatment and diagnostic procedures, it is necessary to transport body fluid from the patient to a remote location. For example, one such procedure is the testing of a sample of body fluid, such as blood, for the glucose concentration level contained therein. Such diagnostic procedures may be conducted clinically or by the patient utilizing a self-testing device or arrangement. There are numerous devices and systems designed to be utilized by the patient for obtaining a sample of blood, and testing the sample to determine the glucose content at a particular point in time. One such system generally includes at least three separate devices. The first device is utilized to draw a sample of blood from the patient by performing a lancing or similar skin piercing operation. Lancets are solid members which do not include a pathway for transporting the sample of blood. Since the lancets do not offer the ability to transport the sample, a separate member or component must be provided for this purpose. Typically, such systems include a separate test strip member which is manually brought into contact with the sample of blood produced by the lancing operation. The sample is then introduced onto the test strip, which includes a mechanism, such as a chemical reagent, for reacting with the blood sample and producing a readable signal. To this end, a separate meter or other reading device is also included in the system. The test strip is typically introduced into the meter, which then interacts with the test strip to produce the quantification of the glucose content contained in the sample of blood.

Such systems suffer from certain drawbacks. The manual operations of lancing, bringing the test strip into contact with the sample of blood thus produced, and the separate step of inserting the test strip into the meter may be difficult to perform for some patients. For instance, diabetics often times suffer from visual impairment as a result of their condition. Thus, it may be difficult for them to locate the sample of blood on the surface of the skin and bring the test strip into communication therewith. Similarly, it may be difficult to properly insert the test strip into the meter. In addition, there is a trend toward minimizing the size of the lancet used to perform the lancing operation in an effort to minimize the pain associated with this self testing procedure, thereby promoting more frequent testing. The use of a smaller gauge lancet also results in a smaller volume of body fluid, or blood, produced by the lancing operation. Such smaller samples of blood may be even more difficult to locate by the patient, and also may be more challenging to transport effectively.

Other systems for self-testing on the market attempt to integrate one or more above described lancing, transporting and quantification operations. One such system requires the user to load a lancet and a test strip into a device, which includes a meter. Once loaded the device is held against the skin and the test initiated by the user, which includes a lancing operation and subsequent transport of a sample of body fluid into the test strip. This arrangement still requires the manual step of loading a separate lancet and test strip correctly into the device, and orienting the device correctly at the surface of the skin in order to perform each test. This device also uses the lancet, which in and of itself does not provide a mechanism to transport the sample of blood. Thus, it is necessary to provide a separate mechanism, which enables transportation of the blood from the surface of the skin to the test strip. In this particular device, the transport function is performed by automatically moving the test strip, which includes capillary channels, into communication with the sample of blood at the surface of the skin. If the test strip is not loaded correctly, or the mechanisms for moving the test strip into position do not function correctly, the device will not function properly. Moreover, the user must purchase, store, handle and load the separate lancet and test strip components for each test. Thus, the successful performance for each test is again at least partially dependent upon the patient correctly associating the lancet and the test strip with the device for each and every test performed.

Yet another conventional self-testing system includes multiple disposable parts for lancing and analyte quantification. In this particular device, a test strip is provided which has an integrated blood transport member in the form of a capillary tube extending from a major planar surface thereof which must be brought into communication with the droplet of blood formed on the surface of the skin resulting from a lancing operation. In order to facilitate the transport function, the test strip is provided with a separate spreading layer sandwiched between the end of the capillary tube and a reagent membrane disposed on an opposing side thereof. The spreading layer facilitates transfer of the blood from the tube to the reagent layer. This system is designed such that a sample volume that completely fills the tube is required in order to obtain an accurate test result. Thus, approximately two micro liters of blood is typically required to be drawn from the patient such that the tube can be completely filled and transferred for further analysis. This requires creation of a wound in the skin large enough to express the necessary volume of blood, thus limiting lancet size reduction efforts. Also, the process of completely filling the tube is time consuming, and may require the user to apply significant efforts to manually express or milk a sufficient quantity of blood from the wound in order to fill the tube. This design also requires the blood to flow through the spreading layer prior to reaching the reagent layer. This two-layer structure is less than optimal from an assembly standpoint (i.e. requiring the assembly of multiple distinct layers), and since the volume of the capillary tube must be first transferred through the spreading layer, this may also have a tendency to slow down the testing procedure and reduce the volume of sample available for analysis. The spreading layer also retains a certain amount of the sample, thereby reducing the amount of the sample that is available for reaction with the reagent layer, and subsequent analysis thereof. Also, the spreading layer can alter certain characteristics of body fluids, such as whole blood.

For instance, the spreading layer may alter the hematocrit contained in a sample of whole blood.

Thus, conventional body fluid transport systems for medical treatment and/or diagnostic procedures suffer certain drawbacks. Such drawbacks include transport operations that are reliant upon the dexterity and ability of the patient to accurately perform various manual procedures. The conventional devices and arrangements also are not fully integrated and require significant intervention on the part of the user in order to perform an accurate test.

SUMMARY OF THE INVENTION

It is, therefore, an object of this invention to provide devices, arrangements and methods for improved transport of a body fluid, such as blood.

According to the current principles of the present invention, one or more of the following advantages may be derived from such devices, arrangements and methods. Consistent with the principles of the present invention, a body fluid can be transported without the necessity of performing various operations or procedures by the patient or user of the device. Thus, for example, it is unnecessary for the patient or user of the device to manually bring a fluid member in communication with a droplet of blood on the surface of skin.

According to the present invention, it is also unnecessary to provide a body fluid sample having a volume at least large enough to fill a capillary tube or other fluid transport member, thus reducing the time necessary to perform a test as well as providing an opportunity to create a smaller wound in the surface of the skin, and/or reducing or eliminating the need to milk blood from the wound, thereby minimizing pain and inconvenience associated with a lancing or other wound creating procedure.

According to the current principles of the invention, improved fluid transport can be provided by associating fluid transport with a fully integrated device. A fully integrated device formed according to the principles of the present invention provides for a potential lower cost device due to a reduction in distinct components which may be sourced from different vendors, which may provide a reduced manufacturing burden (i.e. reduced packaging, assembly, etc.). According to one aspect of the present invention, a needle serves multiple purposes. Namely, the needle acts as a lancet and a transfer tube, all in a single device. This insures that a sterile lancet is used for each and every test, thereby reducing the risk of infection and/or pain associated with lancet reuse, as well as simplified operation.

A further possible advantage provided by the present invention is the elimination of spreading/filtering media or layers. This advantage eliminates the reliance on a special spreading media, which can reduce the volume of blood available to the reagent, thereby providing an opportunity for even greater sample volume reduction and related pain reduction. The elimination of a spreading/filtering media or layer also simplifies manufacturing by reducing the necessity of correctly positioning a small spreading media layer relative to other components of the assembly. The elimination of the spreading layer also prevents the nature of the sample from being influenced thereby, such as an alteration of the hematocrit contained in the sample.

According to one aspect of the present invention, there is provided an arrangement comprising: a base having a bore disposed therein extending from a first surface of the base through a second surface of the base; a fluid transport tube having a first end, a second end opposite the first end, and a lumen having an inner diameter, at least the second end of the tube being received within the bore of the base; at least one fluid transport enhancing groove comprising at least a first section disposed in the second surface of the base and in fluid communication with the bore.

According to a further aspect, the present invention provides a base having a bore disposed therein extending from a first surface of the base through a second surface of the base; a needle having a first end adapted to pierce the skin, a second end opposite the first end, and a lumen having an inner diameter, at least the second end of the tube being received within the bore of the base; at least one fluid transport enhancing groove comprising at least a first section disposed in the second surface of the base and in fluid communication with the bore; and an analyte quantification member in fluid communication with at least one of the bore and the at least one fluid transport enhancing groove.

According to yet another aspect, the present invention provides a wearable blood glucose monitor comprising any of the arrangements described herein.

BRIEF DESCRIPTION OF THE DRAWINGS

The preferred embodiments are illustrated in the drawings in which like reference numerals refer to the like elements and in which:

FIG. 17 is a plan view of a groove arranged according to an alternative embodiment of the present invention.

FIG. 18 is a perspective view of an arrangement of grooves formed according to a further alternative embodiment of the present invention.

DETAILED DESCRIPTION OF THE INVENTION

Devices, arrangements and their associated methods are structured to comprise at least one, or a combination of some or all, of the following characteristics.

Figure 1:
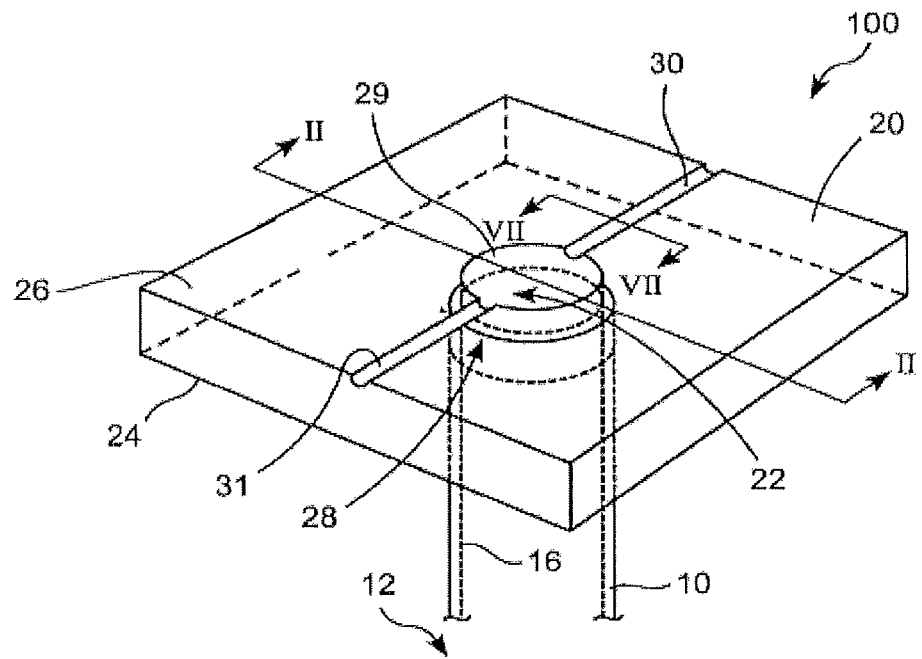
FIG. 1 is a partial perspective view of an arrangement formed according to the present invention.
Figure 2:
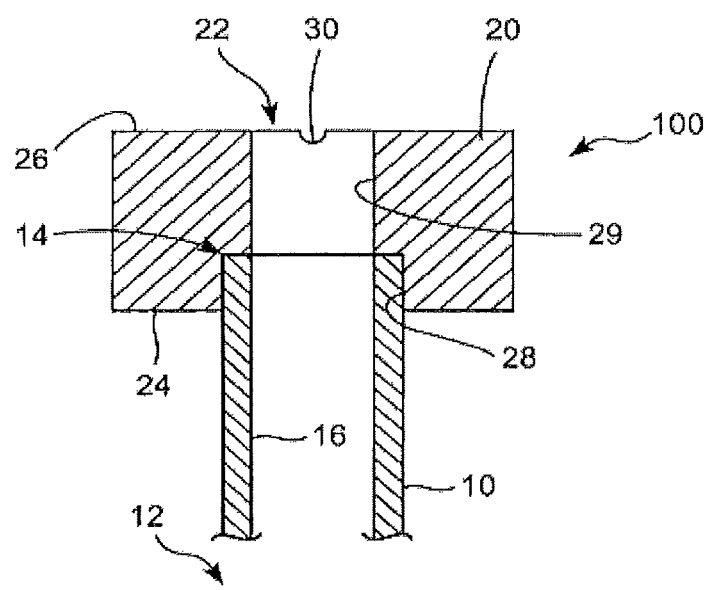
FIG. 2 is a cross sectional view taken along line II-II of FIG. 1.

An exemplary arrangement 100 formed consistent with the principles of the present invention is illustrated in FIGS. 1-2. The arrangement 100 includes a fluid transport tube 10. The fluid transport tube 10 may be formed from any suitable material, such as a metal, glass, or polymeric material. The fluid transport tube 10 may be provided with an inner diameter that is sufficient to produce a capillary action of fluid flowing through the tube. By way of example, the fluid transport 10 may be provided with inner diameter on the order of 0.007 to 0.012 inches. The fluid transport 10 may be provided with a first end 12 and a second end 14 opposite the first end 12. A lumen 16 having an inner diameter, optionally dimensioned as described above, extends along its longitudinal length between the first end 12 and the second end 14. The lumen 16 may be provided, on at least on a portion of the surface thereof, with a fluid flow enhancing feature. For example, such a feature may comprise a suitable coating, such as polydimethylsiloxane (PDMS) or Silwet™. Alternatively, at least a portion of the surface of lumen 16 may be provided with a surface texturing which promotes fluid flow, such as a surface roughening or pattern applied on at least a portion of the surface. According to one embodiment of the present invention, the fluid transport tube 10 is in a form of a needle having a first end provided with a construction adapted to pierce the surface of the skin, such as bevel B or other configuration known in the art (see, e.g., 18 of FIG. 24). The needle may be provided with one or any combination of some or all of the features of the fluid transport tube, as described above.

The arrangement 100 may further include a base 20. The base 20 may have any suitable geometry or size. In the embodiment demonstrated in FIGS. 1-2, the base 20 is in the form of a polygon or block. However, the base 20 of the present invention is not limited to this geometry, and in fact, as illustrated in other embodiments described herein, may have other suitable geometries. Base 20 is formed of any suitable material. According to one embodiment, the base is formed from a material that is more hydrophilic than the tube 10, which will tend to draw the fluid up from the tube. For example, the base 20 can be formed of a metal, glass, quartz, or polymeric material. The base 20 may be provided with a bore 22 that extends from a first surface 24 of the base 20 and through a second surface 26. As illustrated, the base 20 receives at least the second end 14 of the fluid transport tube 10 (or needle 18). According to one embodiment, the bore 22 comprises a first section 28 defining a counter bore for receiving the fluid transport tube 10 or needle at the second end 14 thereof. The fluid transport tube 10 may be secured to the base by any suitable means, such as co-molding, gluing, soldering and the like. According to another embodiment, the bore 22 comprises a second section extending from the counter bore 28, or second end 14 of the tube 10 or needle, to the second surface 26. The above-described portion of the bore 22 is indicated at 29. The second section 29 of the bore 22 may be provided with a fluid flow enhancing feature of the type described above in connection with the lumen 16. The second section 29 of the bore may also be provided with an inner diameter that is substantially the same as the inner diameter of the lumen 16 in order to prevent or minimize unwanted disruptions in the flow of fluid therebetween. In this context, "substantially the same" is intended to encompass surface imperfections and irregularities attributable to the limitations of current common manufacturing techniques. According to a further alternative embodiment, the fluid transport tube 10 or needle 18 may be received in the base 20 such that the second end 14 is substantially is co-planar with the second surface 26 of the base 20 (See, e.g., FIG. 21).

Figure 7A:
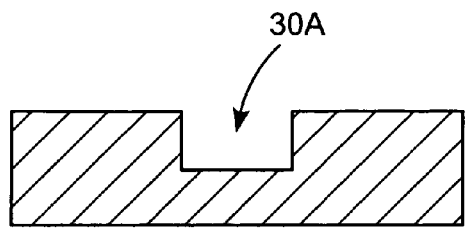
FIGS. 7A-7C are cross-sectional views taken along lines VII-VII of FIGS. 1, 3, and 5, respectively, and represent alternative geometrical cross-sectional configurations of grooves formed according to the principles of the present invention.
Figure 7B:
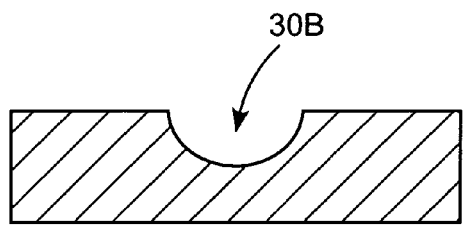
Figure 7C:
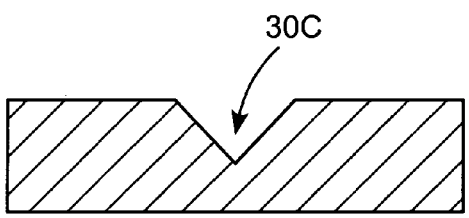

The arrangement 100 includes at least one fluid transport-enhancing groove 30. The fluid transport-enhancing groove 30 is located in the second surface 26 of the base 20. The groove is preferably in fluid communication with the bore 22. The groove 30 may also extend away from the bore 22 to an edge of the second surface 26. The groove 30 may be provided in many different forms. For example, the groove 30 can be provided with a number of suitable geometrical or cross sectional configurations. Non-limiting examples are illustrated in FIGS. 7A-7C. As illustrated in FIG. 7A, grooves 30A formed according to the principles of the present invention may be generally square or rectangular, and comprise a flat bottom. Alternatively, grooves 30B formed according to the present invention may be oval, semi-circular, semi-oval, and the like, and comprise a generally curved bottom. According to a further alternative, groove 30C formed according to the present invention may comprise a generally pointed bottom.

Figure 8:
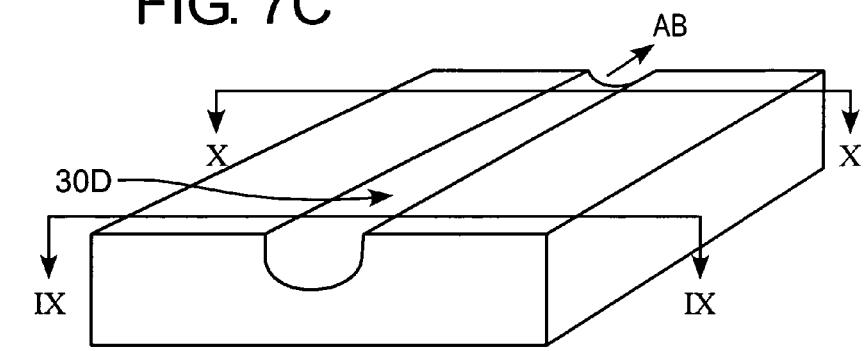
FIG. 8 is a partial perspective view illustrating an alternative groove configured according to the principles of the present invention.
Figure 9:
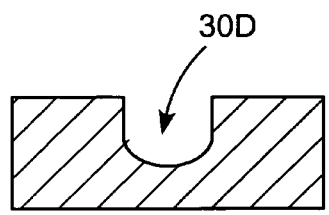
FIG. 9 is a cross-sectional view taken along line IX-IX of FIG. 8
Figure 10:
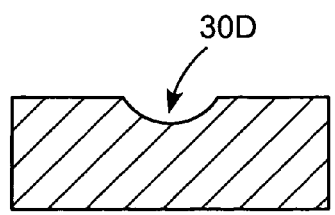
FIG. 10 is a cross-sectional view taken along line X-X of FIG. 8.
Figure 11:
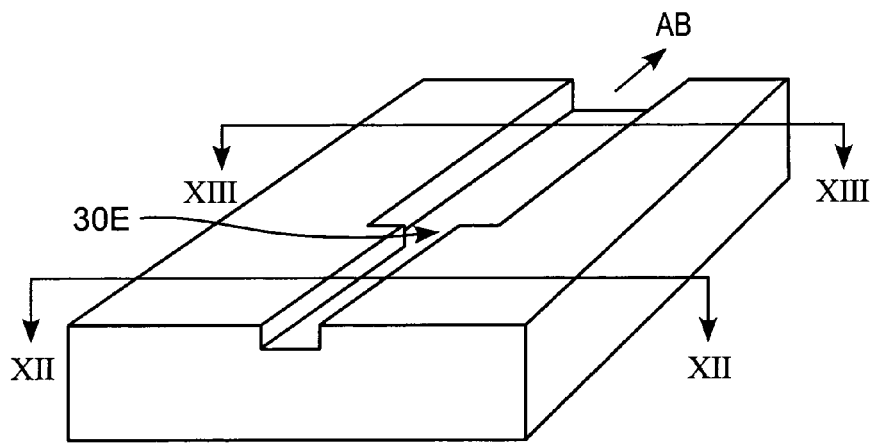
FIG. 11 is a partial perspective view of a groove configured according to a further embodiment of the present invention.
Figure 12:
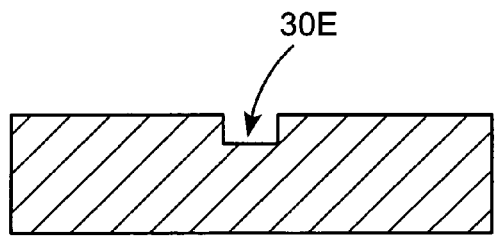
FIG. 12 is a cross-sectional view taken along line XII-XII of FIG. 11.
Figure 13:
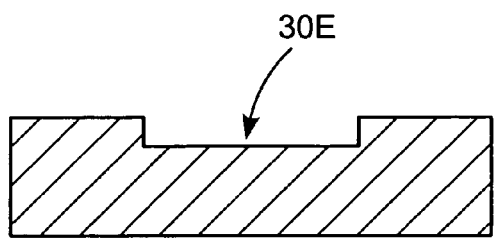
FIG. 13 is a cross-sectional view taken along line XIII-XIII of FIG. 11.

According to a further optional embodiment of the present invention, grooves 30D formed according to the present invention may have a cross sectional area that varies along its length, as illustrated, for example, in FIGS. 8-10. Such a groove 30D is illustrated in FIG. 8. As illustrated therein, the cross sectional area of groove 30D decreases in direction of arrow AB. The direction of arrow AB may correspond to a direction that is generally away from a bore 22. As illustrated by groove 30D in FIGS. 9-10, the cross sectional area is varied by decreasing the depth of the groove along the direction arrow AB. This variation is shown for purposes of illustration only, and the cross sectional area of the groove may be varied by altering other dimensions of the groove, such as its width, as illustrated by groove 30E in FIGS. 11-13. In addition, although the groove 30D of the illustrated embodiment has cross sectional area that decreases in a constant manner along arrow AB, the present invention is not limited to such a configuration. For example, the cross sectional area of a groove formed according the principles of the present invention may change in a step-wise manner, as illustrated by groove 30E. Alternatively, the cross-sectional area of a groove formed according to the present invention may fluctuate along its length, such as in the shape of an hourglass, or repeated hourglass configurations.

Grooves formed according the principles of the present invention may also have any suitable dimensions. In general, grooves formed according to the present invention are dimensioned to provide enhanced capillary action upon contact with target fluid, such as whole blood. For purposes of illustration only, grooves formed according to the present invention, which are square or rectangular may have a depth on the order of 0.002-0.020 inches, and a width of 0.002-0.020 inches. Grooves having a curved bottom may be provided with a radius of curvature on the order of 0.002-0.022 inches.

Grooves formed according the principles of the present invention may also comprise an additional fluid flow-enhancing feature disposed on at least a portion thereof. For example, a groove may be provided with a fluid flow enhancing coating. For example, a coating of polydimethaxelane (PDMS), or Silwet™, may be applied to at least a portion of the groove. Alternatively, or in addition to the aforementioned coating, the groove may be formed in the surface of a material having a flow enhancing property inherent thereto. For example, the groove may be cut into the surface of a hydrophilic polymeric material. Alternatively, or in combination with the above, the groove may also be provided with a surface texturing, which promotes fluid flow therein.

Grooves formed according to the principles of the present invention may be formed by any suitable manufacturing technique. For example, grooves formed according to the present invention may be molded or cast in place. Alternatively, the grooves may be cut, by a suitable removal technique, such as laser ablation, a plunge EDM technique utilizing an electrode whose contour would match the desired groove profile, or another suitable micro-machining technique.

It should be understood that the above discussion of the various characteristics, features, and techniques for forming grooves, applies universally to all the grooves described in the present application regardless of the particular arrangement they may be associated with. Thus, the above discussion will not be repeated in connection with every possible alternative embodiment of the present invention described herein, however, the aforementioned features, characteristics and methods of forming the grooves nonetheless applies to all the embodiments described herein.

As illustrated in FIGS. 1-2 the arrangement 100 may further comprise an additional groove 31 which, for example, may have any of the above-mentioned features and characteristics of the groove 30 or of any of the grooves formed according the principles of the present invention. Thus, the arrangement 100 comprises at least one fluid transport-enhancing groove 30, and may comprise a plurality of such grooves 30, 31.

Figure 3:
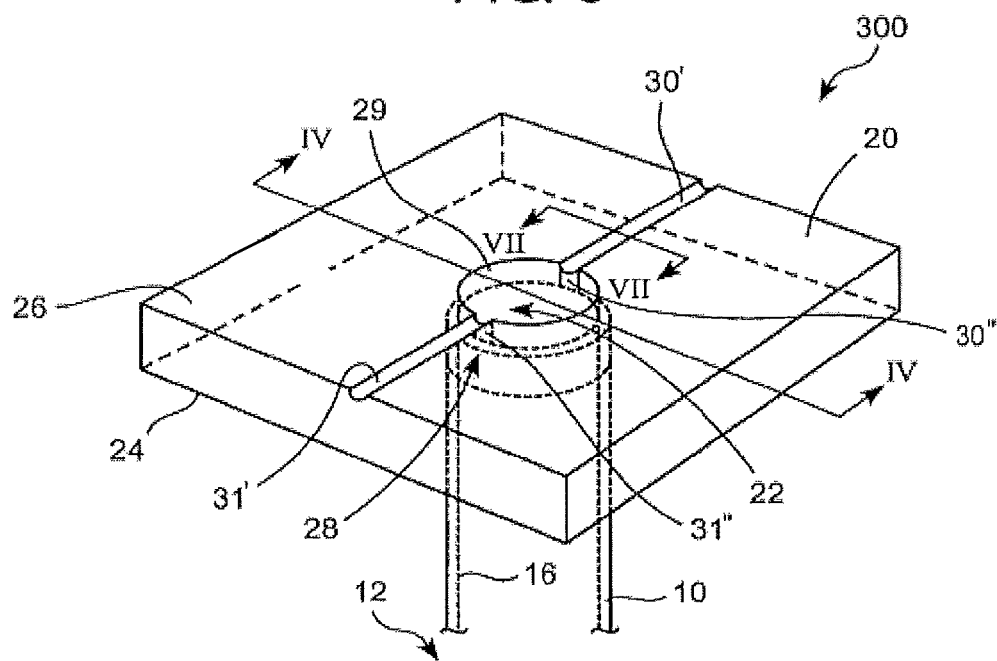
FIG. 3 is a partial perspective view of another arrangement formed according to the present invention.
Figure 4:
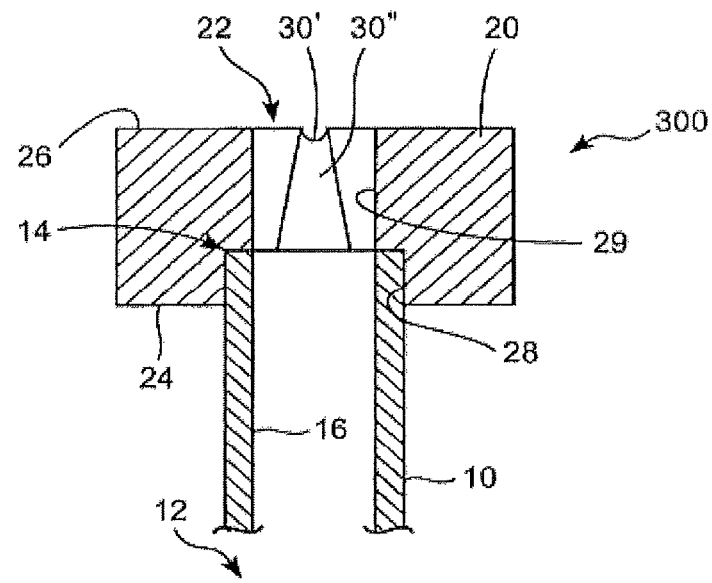
FIG. 4 is a cross-sectional view taken along line IV-IV of FIG. 3.

An alternative arrangement 300 formed according to the principles of the present invention, is illustrated in FIGS. 3-4. The arrangement 300 is similar to the previous described arrangement 100. Thus, discussions of those features which are common to both arrangements 100 and 300 will not be repeated herein. The arrangement 300 is constructed having at least one groove. The at least one groove comprises of first section 30' which extends along the second surface 26 of the base 20, as well as a second section 30" which is provided along the second section 29 of the bore 22. According to the illustrated embodiment, the second section 30" of the groove is substantially linear. Further, according to the illustrated embodiment, the second section 30" extends longitudinally along the second section 29 of the bore 22. The second section 30" can have a substantially constant cross-sectional area along its length, as illustrated in FIG. 3. Alternatively, the second section 30" can be of a varying cross-sectional area that decreases in the direction of desired travel, as illustrated in FIG. 4. According to one embodiment, the largest cross sectional area of the second section 30" is smaller than the cross-sectional area of the lumen 16 to encourage blood to flow into grooves from lumen, then decreases at a constant rate until arriving at a cross-sectional area that is slightly larger than the second section 30" at the transition into the first section 30'. The cross-sectional area of first section 30' can then be a constant size or can vary as previously described herein. The above described alternative construction advantageously creates an increasing gradient of capillary force.

According to the arrangement 300, since the groove originates in the bore 22 at a location which is typically below where a meniscus of the fluid being transported (see, e.g., "M", FIG. 23), such as whole blood, would be located, the second section of the groove 30" acts to promote fluid flow at a location which is closer to the origin of the fluid. The combination of first and second sections of the groove 30', 30" pull the fluid up the groove along the second section 29 of the bore 22, and across the top surface 26 of the base 20 by enhanced capillary action.

The transition between the first and second sections 30', 30" of the groove may have any suitable geometric configuration. According to one alternative embodiment, the transition between the first and second sections 30', 30" is rounded or radiused, so as to minimize adverse impacts on capillary flow between first and second sections 30', 30" of the groove. As illustrated in FIG. 3, the arrangement 300 may also include an additional groove having a first section 31' and a second section 31" that correspond to the sections 30', 30" of the first groove 30.

Figure 5:
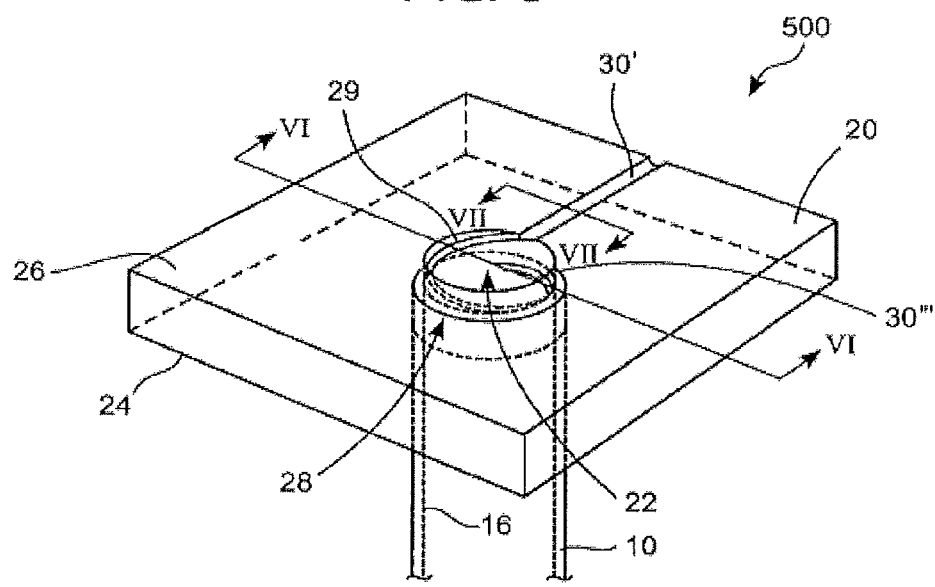
FIG. 5 is a partial perspective view of yet another arrangement formed according to the present invention.
Figure 6:
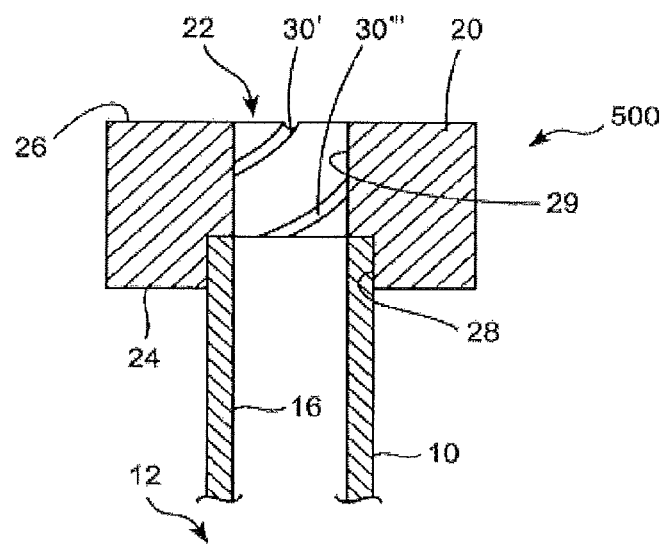
FIG. 6 is a cross-sectional view taken along line VI-VI of FIG. 5.

FIGS. 5 and 6 illustrate a further embodiment of the present invention. As illustrated therein, the arrangement 500 comprises features which are common to the previously described arrangements 100, 300. According to the arrangement 500, the groove comprises a first section 30' which extends along the second surface 26 of the base 20, as well as a second section 30'" which is disposed along the second section 29 of the bore 22. According to this embodiment, the second section 30'" is generally curved. According to the illustrated embodiment, the second section 30'" is provided in the form of a spiral groove disposed along the second section 29 of the bore 22. The location and configuration of the second section 30'" places the fluid enhancing groove at a location which is closer to the meniscus of the fluid, and, in combination with the first section 30' draws fluid up the second section 29, and along the second surface 26, via enhanced capillary action. As with the arrangement 300, the transition between the first and second sections of the groove 30', 30'", may be provided with any suitable geometric configuration. According to one alternative embodiment, this transition is radiused, or curved, so as to minimize adverse impacts on the flow of fluid along the transition between the first and second sections 30', 30'". According to further alternative embodiments, the first and/or second sections may have a cross-sectional area that varies, as previously described.

According to further alternative embodiments of the present invention, the number and arrangement of grooves disposed in the second surface 26 of the base 20 may vary according to the principles of the present invention. Five alternative embodiments of such arrangements are depicted, for purposes of illustration, in FIGS. 14-18.

Figure 14:
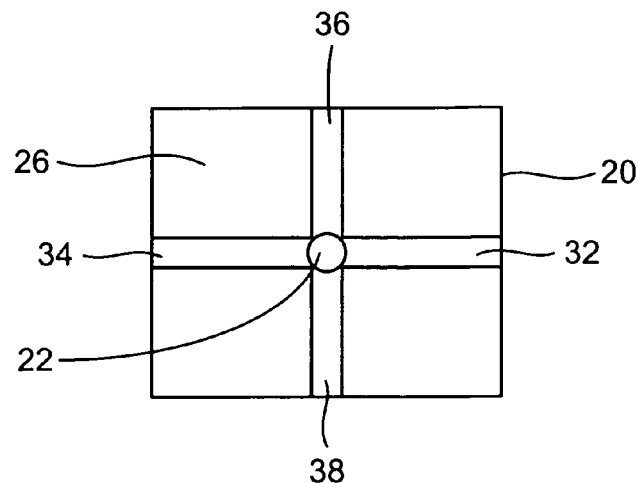
FIG. 14 is a plan view of an arrangement of grooves formed according to the present invention.
Figure 15:
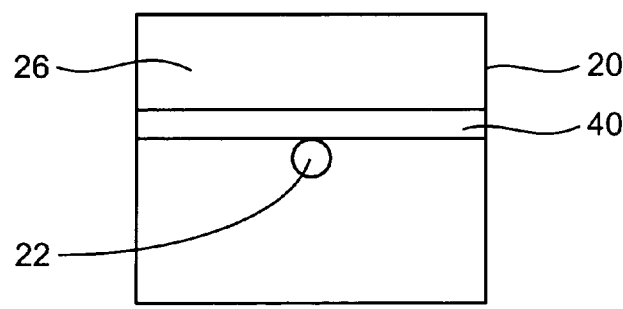
FIG. 15 is a plan view of a groove arranged according to the present invention.

As illustrated in FIG. 14, a plurality of grooves may be provided in the second surface 26 of the base 20, wherein each of the plurality of grooves is in fluid communication at one end thereof with the bore 22, and with an edge of the second surface at an opposing end thereof. According to the illustrated embodiment, grooves 32, 34, 36, 38 are disposed in the second surface in the manner described above. Thus, each of the grooves 32, 34, 36, and 38 intersect, or are in fluid communication with the bore 22 at a first end thereof, and extend to an edge of a second surface 26 at an opposing end thereof.

According to a further alternative, one or more grooves may be provided which are in fluid communication with the bore at a location other than at an end thereof. For example, according to the illustrated embodiment depicted in FIG. 15, at least one groove 40 is provided which tangentially intersects the bore 22 at a location that is intermediate to its ends, and is in fluid communication therewith at this intersection. According to the illustrated embodiment, the groove 40 may be in communication with edges of the second surface 26 at the base 20 at opposing ends thereof. However, it should be understood the present invention contemplates alternatives to this arrangement. For example, the groove 40 may tangentially intersect the bore 22 and have only end thereof in communication with an edge of the second surface 26. In addition, the number of grooves may differ than that of the illustrated embodiment. Thus, for example, it is contemplated that a plurality of grooves may be provided which intersect the bore 22 in a tangential manner.

Figure 16:
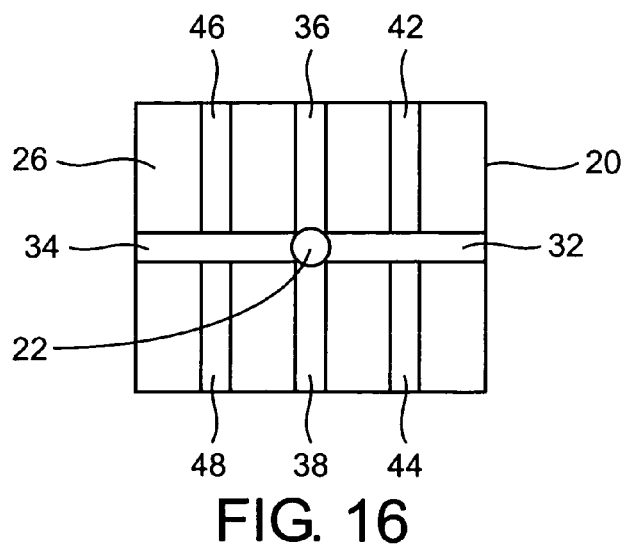
FIG. 16 is a plan view of an arrangement of grooves formed according to the principles of the present invention.

According to the embodiment depicted in FIG. 16, at least one groove may be provided in the surface 26 of the base 20 that intersects, or is in fluid communication with, another groove, but does not directly intersect the bore 22. Thus, for example, as illustrated in FIG. 16, a plurality of grooves 42, 44, 46, 48 are provided which intersect another groove at a first end thereof, and are in communication with an edge of the second surface 26 at an opposing end thereof, but do not otherwise directly intersect the bore 22. Instead, the grooves 32, 34, 36, 38 are in direct fluid communication with the bore 22, thereby enabling fluid communication by the grooves 42, 44, 46, and 48 therewith, albeit in an indirect manner.

As illustrated in FIG. 17, at least one groove 49 may be provided in surface 26 which is in the form of a spiral surrounding, and in fluid communication with, the bore 22. The groove 49 advantageously keeps the body fluid in a location closely centered around a quantification member or assay pad which may be located above the groove 49.

According to another embodiment, a groove pattern 180 such as the one illustrated in FIG. 18 may be provided on surface 26. As illustrated therein, a plurality of fluid transport grooves 182 may be provided in fluid communication with the bore 22 at one end thereof, and with a relatively large groove 184 at the opposing end. The groove 184 surrounds the bore 22. According to the illustrated embodiments, the groove 184 is circular, however, other geometries are contemplated. For example, the groove 184, may be oval or in the form of a polygon. The groove 184 provides a number of advantages. For instance, the groove 184 can collect excess sample volume. This feature may be advantageous where a relatively large volume of body fluid or large volume of blood is acquired during sampling. The groove 184 may optionally be at least partially filled with an absorbent material to facilitate and enhance collection and containment of body fluid therein. A counter bore 186 may also be provided for receiving a quantification member or assay pad. One or more additional vent grooves 188 may be provided in communication with the groove 184 at a first end, and with an edge of the second surface 26. These one or more grooves 188 advantageously allow oxygen to access the groove 184, thereby providing enhanced amounts of oxygen to a quantification member or assay pad in registry therewith. When the assay pad contains a reagent that reacts with an analyte contained in the sample of body fluid, the increased availability of oxygen aids this chemical reaction. The at least one groove 188 may have any suitable form. According to the illustrated embodiment, the at least one groove 188 has a relatively narrow width at the end in communication with the groove 184, and a relatively larger width at the end in communication with the edge of surface 26. Other configurations are contemplated, as previously described herein. As further illustrated, the arrangement 180 may include a plurality of fluid communication grooves 182 in communication with the groove 184 and/or the counter bore 186.

The grooves contained in the arrangement 180 may have any suitable dimensions. According to a non-limiting example, the groove(s) 182 may be approximately 0.002 inches wide and 0.002 inches deep, the groove 184 may be approximately 0.005 inches width and 0.010 inches deep, and the groove(s) 188 may have a width of approximately 0.010 inches at the narrow end, with a depth of approximately 0.010 inches.

As previously noted, the grooves associated with the above embodiments of FIGS. 14-18 may contain any of the previously discussed features, characteristics, and can be manufactured according to the previous generic discussion of the grooves of the present invention. The above described groove configurations may be also be combined with any of the other embodiments and/or arrangements discussed within the present application.

Figure 19:
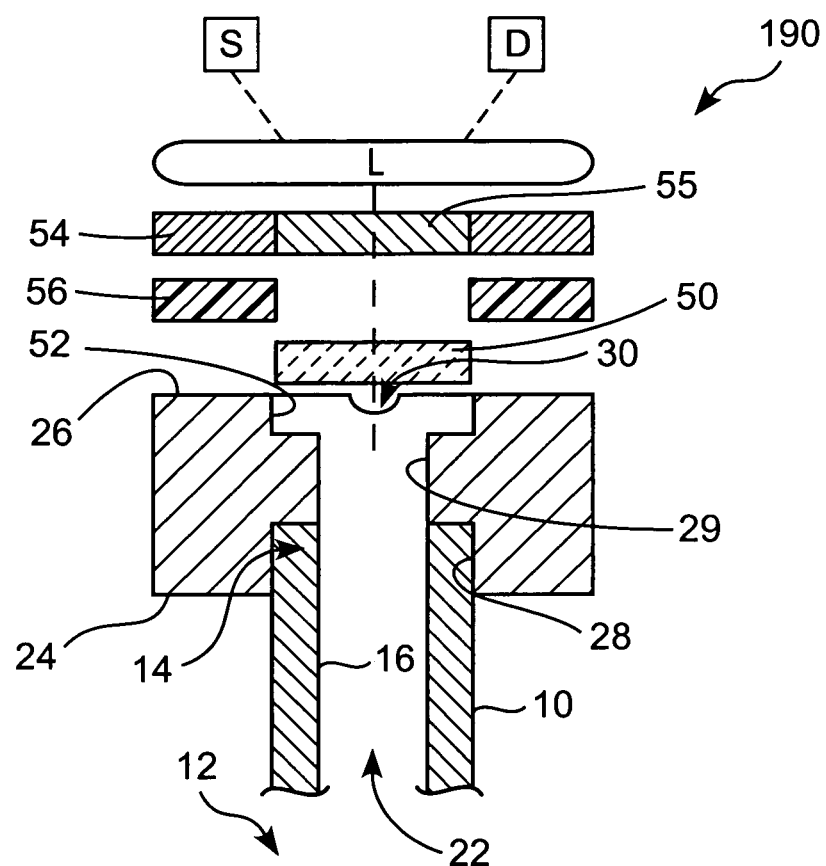
FIG. 19 is a cross-sectional exploded view of an alternative arrangement formed according to the present invention.

Another arrangement 190 constructed according to the principles of the present invention is illustrated in FIG. 19. The arrangement 190 further comprises an analyte quantification member 50. The analyte quantification member 50 may be provided in many different forms. In general, the analyte quantification member 50 may be in the form of a member that provides quantification by any number of suitable techniques, such as electrochemical, or photometric analysis. According to one exemplary embodiment, the analyte quantification member 50 comprises an assay pad or membrane that contains one or more reagents selected to react with a predetermined analyte, thereby producing a readable signal. According to one embodiment of the present invention, the analyte quantification member 50 is in fluid communication with the bore 22. According to a further embodiment, the analyte quantification member 50 is in direct fluid communication with the bore 22. In other words, there are no additional components or features intervening between the bore 22, which opens at the second surface 26, and at least one surface of the analyte quantification member 50. This arrangement is beneficial in that the fluid may be transported from the lumen 16 and/or bore 22 directly to the analyte quantification member 50, thereby enabling a quicker overall fluid transport operation in some arrangements of the prior art, such as those arrangements which include one or more intervening spreading or transfer layers between the analyte quantification member and a fluid transport channel or passageway.

The arrangement 190 may further comprise a means for securing the analyte quantification member 50 to the base 20. Suitable means for securing include an adhesive provided between the analyte quantification member 50 and the base 20, or one or more recess features provided on the base 20 which trap and/or contain the quantification member 50 therein, transparent adhesive tape placed over the quantification member 50 (not shown), or an integral or separate cover member disposed on the base overlying the quantification member 50. According to the illustrated embodiment, the means for securing the analyte quantification member 50 includes a cover 54, which overlies the analyte quantification member 50. The cover 54 may provide means for allowing optical communication with the analyte quantification member 50 lying below. Suitable means for providing optical communication includes forming the cover 54 entirely of a transparent or translucent material. Alternatively, the cover 54 may be formed with one or more windows 55 of a transparent or translucent material, and wherein the cover 54 may otherwise be formed from an opaque material. The cover 54 may be secured to the base 20 by any suitable means. Suitable securing means include fasteners, a press fit, snaps, latches, adhesives, and thermal bonding.

According to the illustrated arrangement 190, an optional spacer 56 may also be provided, which limits compression of the analyte quantification member 50. The optional spacer 56 is preferably formed such that it also permits optical communication with the analyte quantification member 50 lying below. The arrangement 190 may also comprise a counterbore 52 receiving the analyte quantification member 50 therein. This counterbore 52 also limits compression of the analyte quantification member 50 by the cover 54. It should be evident that the arrangement 190 may comprise either the counterbore 52 or the spacer 54 as an effective means of preventing over compression, and need not include both.

The arrangement 190 may further include one or more components typically provided for photometric detection and quantification of the analyte. For example, as illustrated in FIG. 19, a photometric detection arrangement may be provided which includes a light source S, and a detection element D. The detection element D may comprise any suitable arrangement. For example, the detection element D may comprise an array of CMOS-based sensors or detection elements. Optionally, one or more lenses L may be provided as a detection arrangement. As the fluid sample is transported with the assistance of the at least one groove and/or other features described herein, it reaches the quantification member or membrane 50, and a reaction occurs between the target analyte and one or more chemical reagents contained within the membrane 50. This reaction produces a color change in the membrane 50, which can then be detected and analyzed in the arrangement described above, including the light source S, detection element D, and optional lens L, in a manner familiar to those in the art. The present invention contemplates a number of such arrangements. It should be understood that any of the embodiments or arrangements described in the present application may include one or more of the features described in connection with the arrangement 190 described above.

Figure 20:
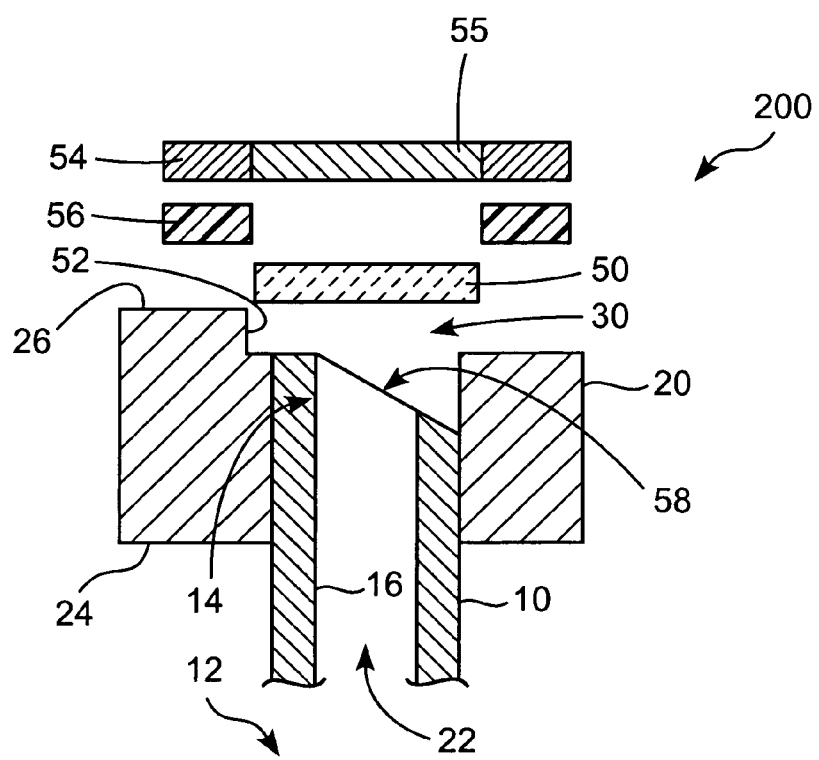
FIG. 20 is a cross-sectional exploded view of yet another alternative arrangement formed according to the present invention.

FIG. 20 illustrates a further alternative arrangement 200 of the present invention. According to the arrangement 200, a counter bore, or first section 28 of the bore 22 is omitted. The second end 14 of the tube 10 or needle is received directly within the bore 22, and extends all the way to a counter bore 52 disposed in the second surface 26 for receiving the analyte quantification member 50 therein. When the counter bore 28 is omitted, and the tube 10 or needle received within the base 20 in the manner previously described, it may be beneficial to provide the second end of the tube 10 or needle with a bevel or taper 58. The bevel or taper 58 is provided to permit more direct access by the fluid flowing within the lumen 16 with the groove 30. It should be evident that the arrangement 200 may comprise either the counterbore 52 or the spacer 54 as an effective means of preventing over compression, and need not include both.

Although not illustrated, the arrangement 200 may also comprise the above-described photometric detection components, such as a light source S, detection element D, and optional lens L as well as any other of the features associated with the previously described embodiments.

Figure 21:
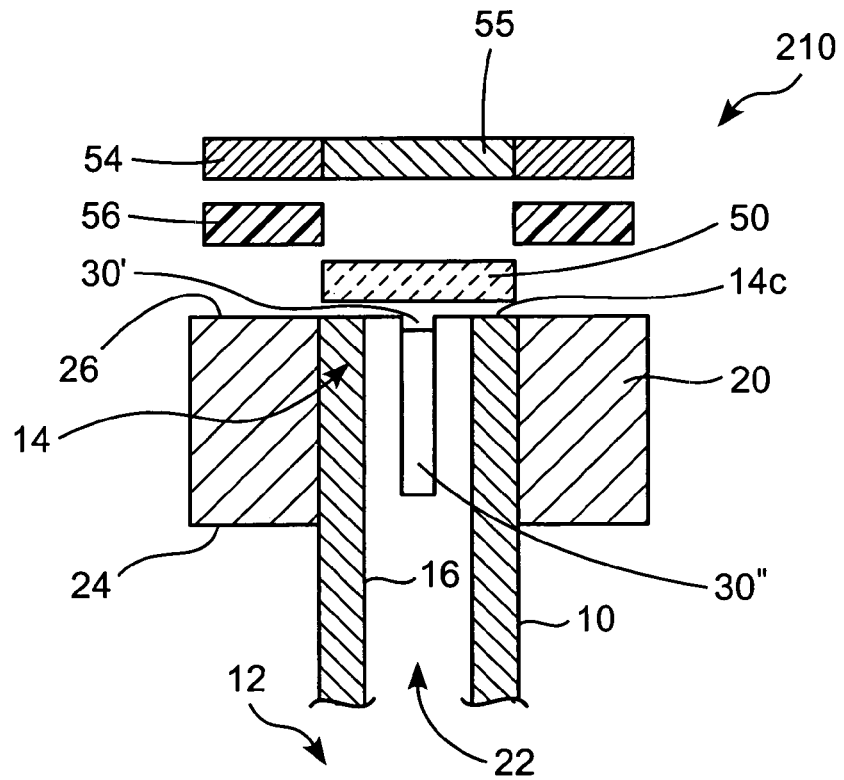
FIG. 21 is a cross-sectional exploded view of a further alternative embodiment of the present invention.
Figure 22:
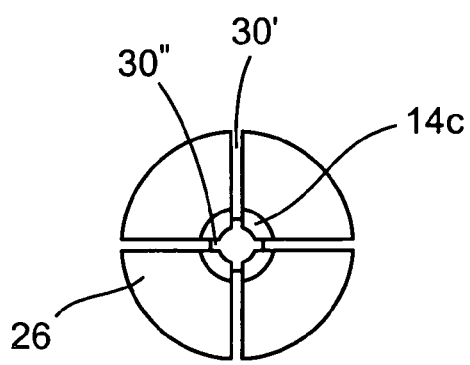
FIG. 22 is a top plan view of the embodiment of FIG. 21.

A modified arrangement 210 formed according to an alternative embodiment of the present invention is illustrated in FIGS. 21-22. As with the arrangement 200, the first section 28 of the bore 22 is omitted. According to the arrangement 210, the counterbore 52 is also omitted and the tube 10 is received within the bore 22 such that the end surface 14c thereof is substantially coplanar with the second surface 26. A quantification member 50 is placed in direct fluid communication with the lumen 16. One or more fluid transport grooves 30' may be provided in the second surface 26. According to the illustrated embodiment, the one or more groove 30' may be present in the end surface 14c of the tube 10 as well as the second surface. As an additional optional feature, the arrangement 210 may further include at least one groove or groove section 30" formed in the lumen 16 of the tube 10. The at least one groove or groove section 30" may be in fluid communication with the least one groove 30', as previously described herein.

Figure 23:
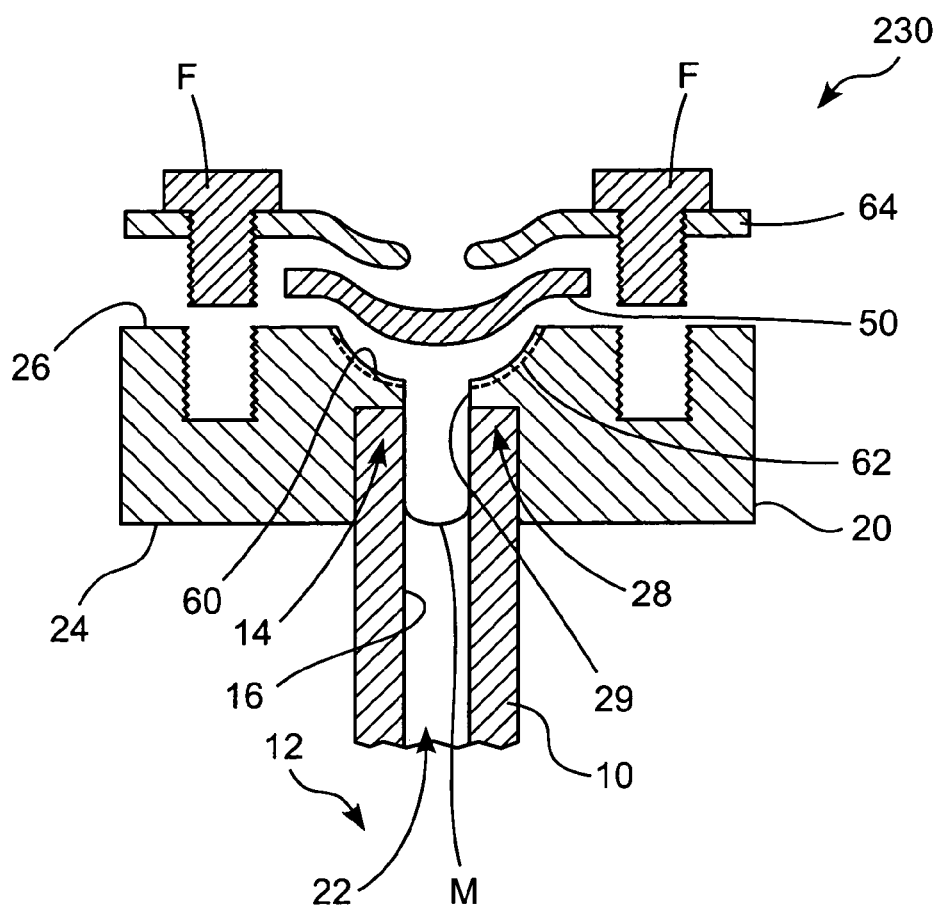
FIG. 23 is a cross-sectional exploded view of an arrangement formed according to an alternative embodiment of the present invention.

A further alternative arrangement of the present invention is illustrated in FIG. 23. The arrangement 230 depicted therein is formed with a counterbore 60 disposed in the second surface 26 of the base 20 for receiving the analyte quantification member 50 therein. As illustrated in FIG. 23, the counter bore 60 is provided with a curved bottom surface. One or more grooves 62, formed as previously described herein, are provided, at least along the curved bottom surface of the counter bore 60, such that they are in fluid communication with at least the second section 29 of the bore 22 at an end thereof. According to the illustrated embodiment, the opposing end of the at least one groove 62 is in communication with an edge of the second surface 26. The arrangement 230 is further provided with a compression member 64, for locating and retaining the analyte quantification member 50. According to the illustrated embodiment, the compression or retention member 64 has a domed or curved configuration so as to mate or generally conform to the curved bottom surface of the counter bore 60. The compression or retention member 64 may be attached to the base by any suitable means, such as those previously described in connection with the cover 54. According to the illustrated embodiment, one or more fasteners F are provided for this purpose.

The arrangement 230 provides certain advantages. For example, if the diameter of the analyte quantification members is larger than the larger diameter of the counter bore 60, the analyte quantification member 50 may still be conformed to and mounted within the counter bore 60, in the manner illustrated in FIG. 23. Since larger analyte quantification members are easier to handle during the manufacturing process, this ability to install an analyte quantification member which is larger in size than may be permitted when using squared counter bored surfaces, provides an efficiency and manufacturing advantage. This arrangement also permits greater tolerances with regard to the precision by which the analyte quantification member 50 is located. Again, this flexibility provides a manufacturing and assembly advantage which may not be possessed by an arrangement having more conventional counterbore structures. Yet another advantage which may be provided by the arrangement 230, includes the fact that as the analyte quantification member or assay pad 50 is compressed within the counter bore 60, it produces a convex curved surface on the bottom thereof, which will extend toward the meniscus of fluid M traveling within the lumen 16 of the tube 10 or needle. Thus, this convex surface of the analyte quantification member 50 is more likely to reach and establish positive contact with a generally concave meniscus M of fluid traveling within the lumen 16.

The arrangement 230 may also be provided with one, or a combination, of the previously described features.

Figure 24:
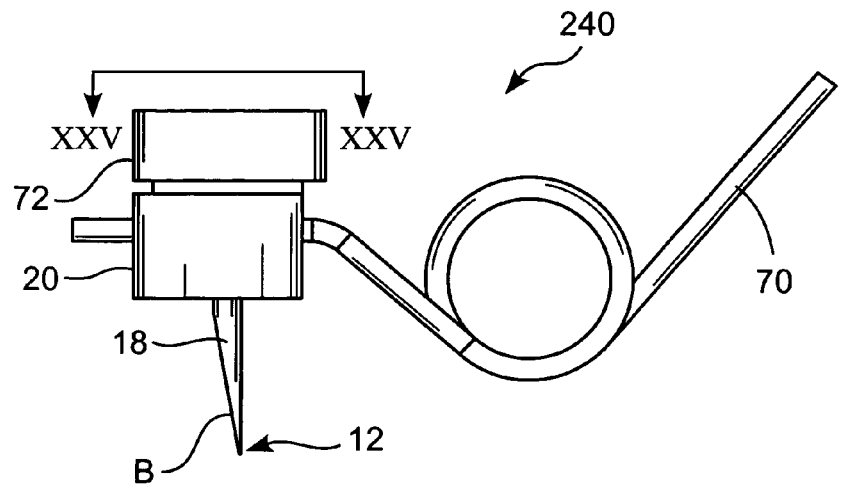
FIG. 24 is a perspective view of an arrangement formed according to a further alternative embodiment of the present invention.
Figure 25:
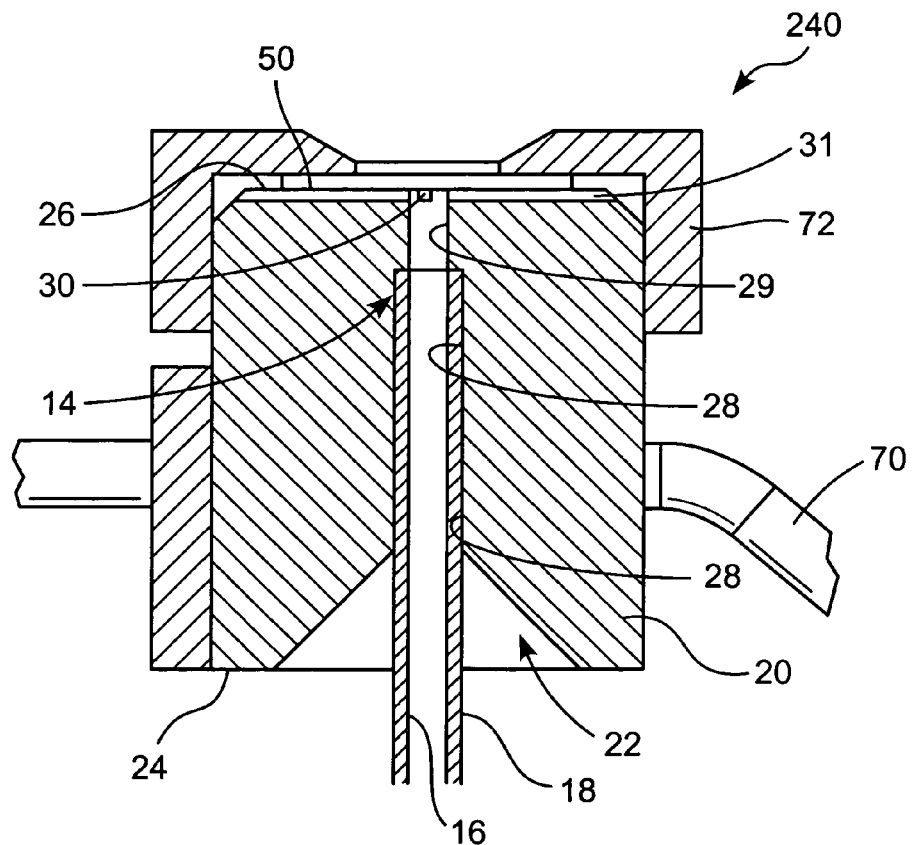
FIG. 25 is a cross-sectional view taken along line XXV-XXV of FIG. 24.

A further alternative arrangement 240 constructed according to the present invention is depicted in FIGS. 24-25. According to the arrangement 240, the base 20 is formed as a generally round hub shaped member having a central bore 22 formed therein. A needle 18 has a first end 12 formed in a manner adapted to pierce the skin. According to the illustrated embodiment, the first end 12 of the needle 18 comprises a bevel B, as common to the art. A second end 14 of the needle 18 is received within a first section 28 of the bore 22. According to the arrangement 240, the hublike base 20 is provided with a second surface 26 having at least one groove 30 formed therein in a manner previously described. According to the illustrated embodiment, the arrangement 240 further comprises at least one additional groove 31 disposed therein, similar to the arrangement depicted in FIG. 1. However, as previously noted herein, numerous alternative groove constructions and arrangements are contemplated. According to the arrangement 240, an analyte quantification member 50 is provided along the second surface 26. In the illustrated embodiment, the analyte quantification member 50 is in direct fluid communication with the second section 29 of the bore 22, thereby providing the advantages previously described herein. A cover in the form of a cap 72 is provided to secure and retain the analyte quantification member 50 to the base 20. As previously discussed herein, alternative devices and arrangements are possible for securing the analyte quantification member 50 to the base 20. According to the illustrated embodiment, the cap may be secured to the base by any suitable means, such as fasteners, a press fit, snaps, latches, adhesives, and/or thermal bonding. The cap 72 is preferably constructed such that it permits optical communication with the analyte quantification member 50 lying below. Thus, the cap 72 may be formed entirely transparent or translucent material. Alternatively, cap 72 may be formed from a generally opaque material having one or more windows disposed therein so as permit the desired optical communication. The arrangement 240 may further comprise a light source, detection element, and/or lens, as previously described herein. In addition, the arrangement 240 may further comprise any of the additional features of any other described arrangements contained herein.

The arrangement 240 may further include an actuation member 70 which is mounted to the base 20 by any suitable mechanism. According to the illustrated embodiment, the actuation member 70 is disposed in a passageway extending through the hublike base 20 (see, e.g., FIG. 25). Any suitable actuation member may be provided according to the arrangement 240. In the illustrated embodiment the actuation member 70 is in the form of torsional spring-type element. Alternative actuation members are contemplated by the present invention.

An integrated device for sampling and testing a sample of body fluid for analyte concentration is formed according to the principles of the present invention may have a number of suitable configurations. According to certain embodiments the device is configured to perform testing by acquiring a sample of blood from the user, transfer the sample to an analysis site, and determine the concentration of glucose contained therein. These operations are all performed with little or no user input. For example, these operations may commence automatically according to a specified or predetermined schedule. Alternatively, these operations may commence at the command of the user via, for example, pressing a start button on the device.

The device may include disposable and reusable portions. The disposable portion may include at least one skin piercing element/transport member and analysis site (which may include an assay pad). The disposable portion may provide the capability to perform a single test. After testing is complete, the disposable portion is discarded and replaced with a new disposable portion before performing another test. Alternatively, the disposable portion includes a plurality of skin piercing elements/transport members and analysis sites. Such disposable units permit a plurality of tests to be performed before it is necessary to discard and replace the disposable unit. The device may be either wearable or handheld, or both.

Figure 26:
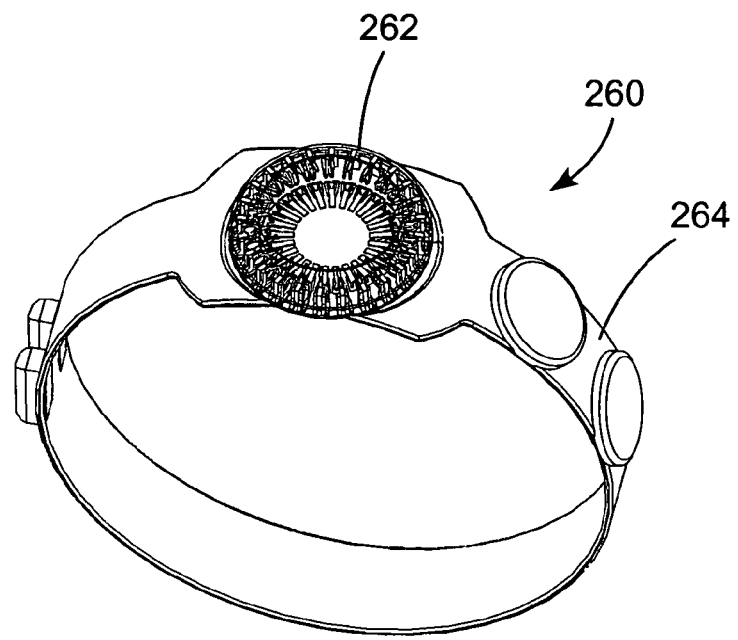
FIG. 26 is a perspective view of a device formed according to a further embodiment of the present invention.
Figure 27:
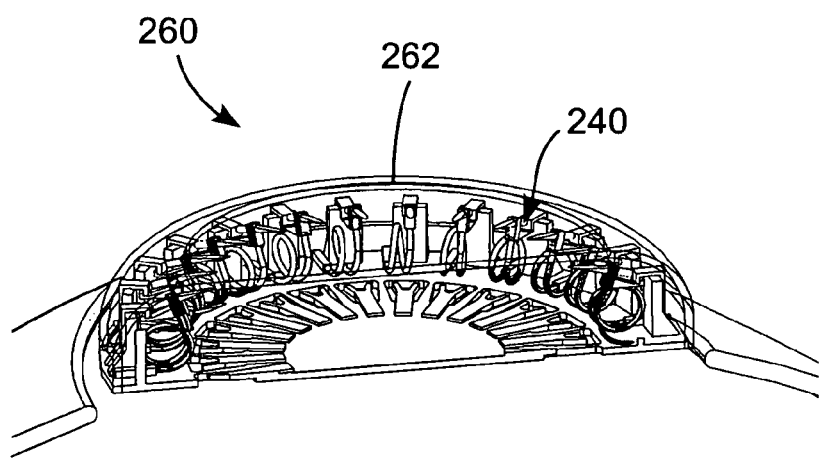
FIG. 27 is a partial cutaway view of the device of FIG. 26.

A non-limiting exemplary integrated device 260 is illustrated in FIGS. 26-27. As illustrated therein the device 260 generally comprises a functional portion 262, and an optional attachment means or band 264. Thus according to the present invention, the integrated device 260 may be wearable. In addition, or alternatively, the integrated device may be operable as a hand-held device. For example, according to the illustrated embodiment, the band 264 can be separated and/or otherwise removed from the user, and the device 260 stored in a suitable case or in the user's pocket. The band can then be grasped and used to hold the device against the skin to perform a testing operation.

The device 260 preferably includes at least one arrangement for performing a measurement of the concentration of an analyte contained in a sample of blood. According to the illustrated embodiment, the device 260 comprises at least one arrangement 240 as described herein comprising at least one skin-piercing element, at least one actuation member, such as a torsional spring element, and at least one analysis site which may contain an assay pad. The at least one arrangement may form part of a disposable portion or unit. According to one embodiment, the disposable unit allows for at least one measurement of the concentration of an analyte contained in a sample of blood prior to being discarded and replaced. According to a further embodiment, the disposable unit allows for a plurality of measurements of the concentration of an analyte contained in a sample of blood prior to being discarded and replaced.

Any of the arrangements and/or embodiments of the present invention may be utilized in devices of the type described above, either entirely or partially. Thus, various combinations of features described in connection with arrangements herein may be selected and utilized independently or together in a multitude of different combinations.

In addition, any of the arrangements described herein may be combined with additional fluid flow enhancing features, such as those described in U.S. Patent Application Publication No. US 2007-0078358, entitled FLUID SAMPLE TRANSPORT DEVICES AND METHODS, the entire content of which is incorporated herein by reference.

All of the above-described exemplary arrangements of the present invention may be used independently, or in combination with other devices and arrangements, and systems. Inclusion in other types of devices, wearable and non-wearable, are specifically contemplated by the present invention. Additional details of such discrete autonomous integrated testing devices may be gathered from the disclosure of U.S. Patent Application Ser. No. 60/721,966, entitled DEVICE FOR FLUID ANALYSIS WITH SAMPLE EXTRACTION AND TRANSPORT, the entire content of which is incorporated herein by reference.

According to the present invention, there is also provided methods for improving the transport of a fluid. The present invention also provides methods for improving the transport of body fluid by enhancing the capillary transport properties of a base or support member.

According to one aspect, the present invention comprises a method of improving transport of a fluid, such as a body fluid, comprising providing a base with a bore disposed therein extending from a first surface of the base through a second surface of the base; providing a fluid transport tube having a first end, a second end opposite the first end, and a lumen having an inner diameter, inserting at least the second end of the tube within the bore of the base; and disposing at least one fluid transport-enhancing groove comprising at least a first section in the second surface of the base such that it is in fluid communication with the bore.

The method may further comprise disposing an analyte quantification member in fluid communication with at least one of the bore and the at least one fluid transport enhancing groove. The quantification member may be located such that it is in direct fluid communication with at least one of the bore and the at least one fluid transport enhancing groove. The quantification member can comprise a fibrous membrane or assay pad containing a chemical reagent chosen to react with a predetermined analyte. The method may further include providing a cover overlying the quantification member. The cover can be constructed to permit optical communication with the quantification member. The cover may also be in the form of a cap. Methods of the present invention may further comprise providing a spacer interposed between the quantification member and the cover. A counterbore may also be formed in the second surface of the base receiving the quantification member therein. The counter bore may have at least one of a flat bottom and a curved bottom.

The method may further include providing the fluid transport tube in the front of a needle, wherein the first end of the needle is constructed for piercing the skin. The needle can be formed from a metal, and the base is formed, at least in part from a metal, a polymer, a glass, or a ceramic.

In any of the above-described methods, at least a portion of the lumen may comprise a fluid transport enhancing feature, such as at least one of a coating and a surface texture.

The methods of the present invention may include providing the bore with a first section extending from the first surface of the base and defining a counter bore receiving at least the second end of the fluid transport tube. The bore may also comprise a second section extending from the second end of the fluid transport tube to the second surface of the base.

In any of the above described methods, the at least one fluid transport enhancing groove may further comprise a second section disposed in the second section of the bore. The second section of the at least one groove can be substantially linear and extend longitudinally along the second section of the bore, or may be formed substantially as a spiral in the second section of the bore.

According to the methods of the present invention, at least one of the first and second sections of the groove can be provided with a geometrical cross-sectional configuration comprising a flat-bottomed groove, a curved-bottom groove, or a pointed-bottom groove. Optionally, at least one of the first and second sections of the groove comprises a cross-sectional area that decreases in the direction extending away from the second end of the needle.

Methods performed according to the present invention may further comprise providing a plurality of fluid transport enhancing grooves in the second surface of the base, and wherein at least two of the plurality of grooves may intersect the bore at the second surface of the base. The plurality of grooves may further comprise at least one groove disposed in the second surface of the base that intersects another of the plurality of grooves, but does not intersect the bore. Alternatively, or in addition, the at least one groove may tangentially intersect the bore along the second surface of the base. At least one of the first and second sections of the groove(s) may comprise a fluid transport-enhancing feature, the feature comprising at least one of a coating and a surface texture. The portion of the bore extending from the second end of the tube to the second surface may comprise an additional fluid transport enhancing feature, the feature comprising at least one of a coating and a surface texture.

According to the methods of the present invention, the base may comprise a generally cylindrical hub. An actuation member may be attached to the hub.

According to an alternative aspect of the present invention, a method for improving transport of a fluid, such as a body fluid, comprises providing a base having a bore disposed therein extending from a first surface of the base through a second surface of the base; providing a needle having a first end adapted to pierce the skin, a second end opposite the first end, and a lumen having an inner diameter, inserting at least the second end of the tube received within the bore of the base; disposing at least one fluid transport enhancing groove comprising at least a first section disposed in the second surface of the base in fluid communication with the bore; and providing an analyte quantification member in fluid communication with at least one of the bore and the at least one fluid transport enhancing groove.

According to the methods of the present invention, a wearable or hand held blood glucose monitor is formed and/or operated by a method comprising, at least in part, any of the above described methods.

While this invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. §112, ¶6.

We claim:
1. An arrangement comprising:
a base having a bore disposed therein extending from a first surface of the base through a second surface of the base;
a fluid transport tube having
a first end configured to receive a fluid sample,
a second end opposite the first end and positioned within the bore, and
a lumen having an inner diameter;
a plurality of transport-enhancing grooves formed in the second surface of the base, wherein each of the plurality of transport-enhancing grooves intersects the bore and is in fluid communication with the bore; and
an analyte quantification member,
wherein the analyte quantification member is in contact with the second surface of the base and is in direct fluid communication with the bore, wherein the analyte quantification member directly overlies the bore and directly overlies at least a portion of each of the-plurality of transport-enhancing grooves.

2. The arrangement of claim 1, wherein the fluid transport tube comprises a needle and the first end of the needle is constructed for piercing skin.

3. The arrangement of claim 2, wherein the needle is formed from a metal, and the base is formed, at least in part, from a metal, a polymer, a glass, or a ceramic.

4. The arrangement of claim 1, wherein at least a portion of the lumen comprises at least one of a coating and a surface texture.

5. The arrangement of claim 1, wherein the bore comprises a first section extending from the first surface of the base and defining a counterbore receiving at least the second end of the fluid transport tube.

6. The arrangement of claim 5, wherein the bore further comprises a second section extending from the second end of the fluid transport tube to the second surface of the base.

7. The arrangement of claim 6, wherein the bore further comprises a first fluid transport enhancing feature located in at least the second section of the bore.

8. The arrangement of claim 7, wherein the first fluid transport enhancing feature extends longitudinally along the second section of the bore.

9. The arrangement of claim 7, wherein the first fluid transport enhancing feature comprises a spiral groove in the second section of the bore.

10. The arrangement of claim 7, wherein the first fluid transport enhancing feature has a width that decreases in a direction toward the second surface.

11. The arrangement of claim 6, wherein the second section of the bore comprises at least one of a coating and a surface texture.

12. The arrangement of claim 1, wherein the analyte quantification member comprises an assay pad containing a chemical reagent configured to react with a predetermined analyte.

13. The arrangement of claim 1, further comprising a cover overlying the analyte quantification member.

14. The arrangement of claim 13, wherein the cover is constructed to permit optical communication with the analyte quantification member.

15. The arrangement of claim 13, wherein the cover is in the form of a cap.

16. The arrangement of claim 13, further comprising a spacer interposed between the analyte quantification member and the cover.

17. The arrangement of claim 1, further comprising at least one fluid transport enhancing groove in the fluid transport tube.

18. The arrangement of claim 1, wherein the base comprises a hub.

19. The arrangement of claim 18, further comprising an actuation member attached to the hub.

20. The arrangement of claim 1, wherein the base is formed from a material that is more hydrophilic than the fluid transport tube.

21. The arrangement of claim 1, wherein the arrangement lacks a spreading layer.

22. An integrated analyte detector device comprising the arrangement of claim 1.

23. The device of claim 22, wherein the device is configured to be wearable or handheld.

24. The device of claim 23, wherein the device is constructed to perform at least one blood glucose concentration measurement.

25. The device of claim 24, wherein the device is constructed to perform multiple blood glucose concentration measurements.

26. An arrangement comprising:
a base having a bore disposed therein extending from a first surface of the base through a second surface of the base;
a needle having
a first end adapted to pierce skin,
a second end opposite the first end and positioned within the bore, and
a lumen having an inner diameter;
a plurality of transport-enhancing grooves formed in the second surface of the base, wherein each of the plurality of transport-enhancing grooves intersects the bore and is in fluid communication with the bore; and
an analyte quantification member,
wherein the analyte quantification member is in contact with the second surface of the base and is in direct fluid communication with the bore,
wherein the analyte quantification member directly overlies the bore and directly overlies at least a portion of each of the plurality of transport-enhancing grooves.

27. The arrangement of claim 26, wherein the base is formed from a material that is more hydrophilic than the needle.

28. The arrangement of claim 26, wherein the plurality of transport-enhancing grooves comprise at least one of a coating and a surface texturing.

29. The arrangement of claim 26, wherein the arrangement lacks a spreading layer.

30. An integrated analyte detector device comprising the arrangement of claim 26.

31. The device of claim 30, wherein the device is configured to be wearable or handheld.

32. The device of claim 31, wherein the device is constructed to perform at least one blood glucose concentration measurement.

33. The device of claim 32, wherein the device is constructed to perform multiple blood glucose concentration measurements.

* * * * *